(12) United States Patent
Tsuji

(10) Patent No.: US 9,101,328 B2
(45) Date of Patent: Aug. 11, 2015

(54) RADIATION IMAGING APPARATUS AND CONTROL METHOD THEREOF, AND RADIATION IMAGING SYSTEM

(71) Applicant: FUJIFILM Corporation, Tokyo (JP)

(72) Inventor: Tetsuya Tsuji, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 253 days.

(21) Appl. No.: 13/754,270

(22) Filed: Jan. 30, 2013

(65) Prior Publication Data

US 2013/0202086 A1 Aug. 8, 2013

(30) Foreign Application Priority Data

Feb. 3, 2012 (JP) ................................ 2012-021868

(51) Int. Cl.
*H05G 1/44* (2006.01)
*H05G 1/56* (2006.01)
(Continued)

(52) U.S. Cl.
CPC ............ *A61B 6/542* (2013.01); *A61B 6/4233* (2013.01); *A61B 6/52* (2013.01); *A61B 6/548* (2013.01); *G01T 1/026* (2013.01); *G01T 1/1603* (2013.01); *H05G 1/44* (2013.01); *H05G 1/56* (2013.01);
(Continued)

(58) Field of Classification Search
CPC ............ H05G 1/00; H05G 1/02; H05G 1/08; H05G 1/085; H05G 1/26; H05G 1/30; H05G 1/32; H05G 1/38; H05G 1/42; H05G 1/44; H05G 1/46; H05G 1/56; G01T 1/00; G01T 1/02; G01T 1/023; G01T 1/026; G01T 1/15; G01T 1/16; G01T 1/1603; G01T 1/24; G01T 1/246; G01T 1/247; G01T 7/005
See application file for complete search history.

(56) References Cited

U.S. PATENT DOCUMENTS 5,812,191 A * 9/1998 Orava et al. .................... 348/308
7,433,445 B2 10/2008 Okada et al.
(Continued)

FOREIGN PATENT DOCUMENTS

JP 8-186762 A 7/1996
JP 9-55298 A 2/1997
(Continued)

OTHER PUBLICATIONS

Japanese Office Action dated Mar. 26, 2014, issued in corresponding Japanese Patent Application No. 2013-012201.
(Continued)

*Primary Examiner* — Anastasia Midkiff
(74) *Attorney, Agent, or Firm* — Birch, Stewart, Kolasch & Birch, LLP

(57) ABSTRACT

An FPD detects an X-ray image of an object. The FPD includes a plurality of pixels arranged in its image capturing field. Each pixel receives X-rays emitted from an X-ray source, and outputs a pixel value in accordance with an X-ray dose applied thereto. A pixel determiner determines a minimum-value pixel out of the pixels based on the pixel values of the pixels. The minimum-value pixel is a pixel whose pixel value is the lowest. The pixel determiner sets the minimum-value pixel as an exposure control pixel. A comparator compares a first integrated value, which is an integrated value of the pixel values of the minimum-value pixel, with a predetermined first threshold value. The comparator performs X-ray emission control such that, when the first integrated value has reached the first threshold value, the X-ray source stops emitting the X-rays.

16 Claims, 17 Drawing Sheets

(51) Int. Cl.
*G01T 1/02* (2006.01)
*A61B 6/00* (2006.01)
*G01T 1/16* (2006.01)
*H05G 1/38* (2006.01)
*G01T 7/00* (2006.01)
*G01T 1/24* (2006.01)

(52) U.S. Cl.
CPC .............. *A61B 6/4283* (2013.01); *G01T 1/02* (2013.01); *G01T 1/247* (2013.01); *G01T 7/005* (2013.01); *H05G 1/38* (2013.01)

(56) References Cited

U.S. PATENT DOCUMENTS

| | | | |
|---|---|---|---|
| 2005/0169425 A1* | 8/2005 | Takasawa | 378/97 |
| 2008/0226024 A1 | 9/2008 | Strommer | |
| 2013/0058456 A1* | 3/2013 | Kuwabara et al. | 378/62 |
| 2013/0121464 A1* | 5/2013 | Tajima | 378/62 |
| 2013/0136233 A1* | 5/2013 | Okada | 378/62 |

FOREIGN PATENT DOCUMENTS

| | | |
|---|---|---|
| JP | 2003-529425 A | 10/2003 |
| JP | 2004-344249 A | 12/2004 |
| JP | 2010-213768 A | 9/2010 |
| JP | 2011-10884 A | 1/2011 |
| JP | 2012-15913 A | 1/2012 |
| WO | WO 01/76228 A1 | 10/2001 |

OTHER PUBLICATIONS

European Search Report dated May 3, 2013 issued in European Patent Application No. 13153242.6.
European Office Action issued on Jul. 23, 2014 in corresponding EuropeanPatent Application No. 13153242.6.

* cited by examiner

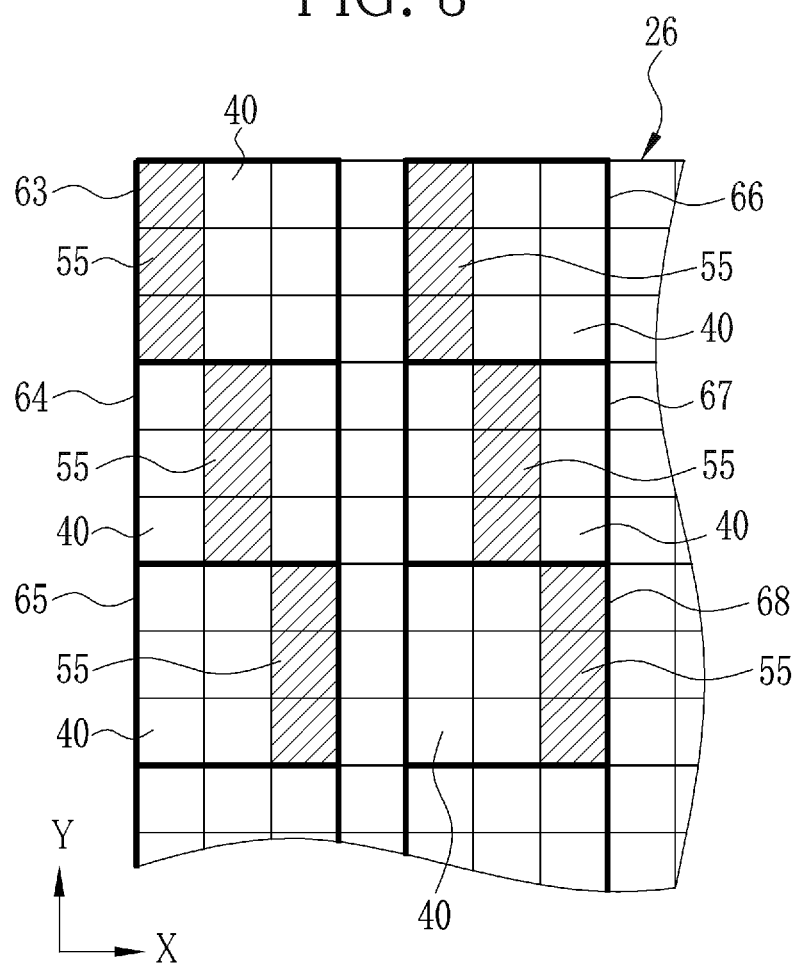

PROFILE OF CHEST RADIOGRAPHY
IN LATERAL DIRECTION
(WITHOUT IMPLANT)

PROFILE OF CHEST RADIOGRAPHY
IN LATERAL DIRECTION
(WITH IMPLANT)

RADIATION IMAGING APPARATUS AND CONTROL METHOD THEREOF, AND RADIATION IMAGING SYSTEM

BACKGROUND OF THE INVENTION

1. Field of the Invention

The present invention relates to a radiation imaging apparatus for taking a radiographic image from radiation passed through an object, a control method of the radiation imaging apparatus, and a radiation imaging system having the radiation imaging apparatus.

2. Description Related to the Prior Art

In a medical field, a radiation imaging system, for example, an X-ray imaging system using X-rays is widely known. The X-ray imaging system is constituted of an X-ray generating apparatus for applying the X-rays to an object (a body portion, for example, a chest of a patient), and an X-ray imaging apparatus for taking an X-ray image by reception of the X-rays passed through the object.

In recent years, the X-ray imaging apparatus that uses a flat panel detector (FPD) as a detection panel, instead of an X-ray film or an imaging plate (IP), becomes widespread. The FPD has a matrix of pixels each of which produces and accumulates signal charge in accordance with an X-ray dose applied thereto. The FPD converts the signal charge of the pixels into a voltage signal by its signal processing circuit. Thereby, the FPD electrically detects the X-ray image, and outputs the X-ray image as digital image data.

With the aim of reducing X-ray exposure of a patient and improving X-ray image quality, some X-ray imaging systems have an automatic exposure control (AEC) function for automatic control of an X-ray dose. For example, Japanese Patent Laid-Open Publication No. 09-055298 discloses an X-ray fluoroscopic apparatus having a video camera, being an image detector, and an image intensifier disposed in front of the video camera. In this apparatus, the image intensifier converts an X-ray image into an optical image, and the video camera captures a moving image to be displayed on a monitor. The image intensifier is in the shape of a rectangle, and is provided with three intensity detection sensors that are disposed at the middle of an upper portion of the rectangle and at the right and left of a lower portion of the rectangle, respectively, as X-ray sensors for detecting the X-ray dose. The video camera captures the moving image of an object in observation, so a fluoroscopic image is displayed on the monitor. During the display (fluoroscopy), pixel values of the fluoroscopic image are detected and a histogram of the pixel values is produced in each individual area corresponding to the position of each X-ray sensor. Based on the histograms, an unexposed area to which no X-ray is applied, an object area, and a directly exposed area to which the X-rays are directly applied without through the object are determined. Out of the three X-ray sensors, the one disposed in the object area is chosen. In taking an X-ray image by use of an X-ray film, X-ray exposure time is controlled based on the X-ray dose detected by the chosen X-ray sensor.

Also, U.S. Pat. No. 7,433,445 discloses a radiation imaging apparatus for mammography. This apparatus includes an image detector composed of an FPD, and an exposure control sensor disposed in a position corresponding to an outer edge of the image detector. In this apparatus, an X-ray dose (necessary dose) necessary for obtaining desirable image equality is calculated from the thickness of an object, X-ray absorptance, and the like, prior to performing mammography. During the mammography, an X-ray dose (detected dose) detected by the exposure control sensor is compared with the necessary dose. When the detected dose has reached the necessary dose, X-ray emission is stopped.

The X-ray fluoroscopic apparatus of the Japanese Patent Laid-Open Publication No. 09-055298 is provided with the plurality of X-ray sensors for use in AEC. The X-ray sensors are used for identification of the object area, out of the three areas of the unexposed area, the object area, and the directly exposed area. The X-ray sensor has low spatial resolution, and its detection surface has fixed size and is in a fixed position. Depending on the type, size, shape, or the like of a body portion, there may be cases where AEC cannot be performed appropriately, and desirable image quality cannot be obtained.

This is because, for example, in chest radiography, the object area includes lung fields, a mediastinum, and a diaphragm that have different X-ray transmittances from each other. The difference in the X-ray transmittance causes variations in the X-ray dose to be transmitted. Therefore, the image quality differs depending on which part is used for detecting the X-ray dose as a reference of AEC. In general, the higher the density, the finer the graininess of an X-ray image would be. Thus, a part having a low X-ray transmittance is more preferably used for detecting the X-ray dose than a part having a high X-ray transmittance, because increase in the density of the entire image facilitates improving the image quality.

However, in the Japanese Patent Laid-Open Publication No. 09-055298, the plurality of X-ray sensors are disposed in the fixed positions, and have the fixed size and the low spatial resolution. Thus, the X-ray sensors may not be able to detect the X-ray dose at an appropriate position in the object area, depending on the type, size, shape, or the like of the body portion. Therefore, the apparatus of the Japanese Patent Laid-Open Publication No. 09-055298 may fail to perform AEC appropriately, depending on the type, size, shape, or the like of the body portion.

On the other hand, in the U.S. Pat. No. 7,433,445, there is only one exposure control sensor provided at the outer edge of the image detector, and its detection surface has fixed size and position. Thus, as with the Japanese Patent Laid-Open Publication No. 09-055298, the apparatus of the U.S. Pat. No. 7,433,445 may fail to perform appropriate AEC depending on the type, size, shape, or the like of the body portion, and fail to obtain favorable image quality.

Furthermore, both the X-ray sensors of the Japanese Patent Laid-Open Publication No. 09-055298 and the exposure control sensor of the U.S. Pat. No. 7,433,445 are provided separately from the image detector (video camera or FPD), and hence may cause complex structure.

SUMMARY OF THE INVENTION

An object of the present invention is to provide a radiation imaging apparatus that has structure simpler than ever and can take a radiographic image of favorable image quality irrespective of a body portion to be imaged, a control method of the radiation imaging apparatus, and a radiation imaging system having the radiation imaging apparatus.

To achieve the above and other objects of the present invention, a radiation imaging apparatus according to the present invention includes an image detector, a pixel determiner, and a comparator. The image detector, which detects a radiographic image of an object, includes a plurality of pixels arranged in an image capturing field. Each of the pixels receives radiation emitted from a radiation source and outputs a pixel value in accordance with a received radiation dose. The pixel determiner determines at least one typical low-value pixel from the pixels based on the pixel values, and sets the typical low-value pixel as an exposure control pixel. The comparator compares a first integrated value being an integrated value of the pixel value of the typical low-value pixel with a predetermined first threshold value, and performs radiation emission control such that, when the first integrated value has reached the first threshold value, the radiation source stops emitting the radiation.

The pixel determiner preferably determines at least one typical high-value pixel from the pixels based on the pixel values, and sets the typical high-value pixel as another exposure control pixel. The comparator preferably compares a second integrated value being an integrated value of the pixel value of the typical high-value pixel with a predetermined second threshold value, and performs the radiation emission control such that, when the second integrated value has reached the second threshold value, the radiation source stops emitting the radiation even if the first integrated value has not reached the first threshold value.

The radiation imaging apparatus preferably further includes an irradiation field determiner for determining an irradiation field, which is a field irradiated with the radiation in the image capturing field, based on the pixel values. The pixel determiner preferably determines in the irradiation field a directly exposed area being an area applied with the radiation directly without through the object, an implant area being an area of an implant implanted in the object, and an object area being an area excluding the directly exposed area and the implant area from the irradiation field. The typical low-value and high-value pixels are preferably determined out of the pixels in the object area.

The pixel determiner preferably determines the object area based on a histogram of the pixel values of the pixels in the irradiation field.

The pixel determiner may determine the typical low-value pixel out of the pixels present within an index area, which is predetermined in the image capturing field in accordance with a body portion to be imaged.

The pixel determiner may determine the typical high-value pixel out of the pixels present within an interest area, which is predetermined in the image capturing field in accordance with the body portion to be imaged.

It is preferable that radiation absorptance is higher in the index area than in the interest area.

The pixels may include a plurality of normal pixels for specific use in detection of the radiographic image, and a plurality of detection pixels distributed throughout the image capturing field to detect the radiation dose.

The radiation imaging apparatus may further include a pixel value estimator for estimating the pixel value of the normal pixel based on the pixel values of the detection pixels near the normal pixel to be estimated. The pixel determiner preferably determines the typical low-value and high-value pixels based on the estimated pixel values.

The image detector may have a plurality of pixel groups each including one or more normal pixels and one or more detection pixels. The detection pixels are laid out differently between the pixel groups adjoining to each other. The pixel value estimator may estimate the pixel value of the normal pixel of a first pixel group, based on the pixel value of the detection pixel belonging to the first pixel group and the pixel value of the detection pixel belonging to a second pixel group adjoining to the first pixel group.

The pixel determiner may determine the typical low-value and high-value pixels out of the detection pixels.

Signal lines electrically connected to the pixels may be routed in the image capturing field to output the pixel values.

The detection pixel may be connected to the signal line directly or through a switching element.

The pixels may include a combined pixel that is composed of a first subpixel functioning as the normal pixel and a second subpixel functioning as the detection pixel.

A radiation imaging system of the present invention includes a radiation generating apparatus and a radiation imaging apparatus. The radiation generating apparatus includes a radiation source for emitting radiation to an object, and a source controller for controlling operation of the radiation source. The radiation imaging apparatus includes an image detector, a pixel determiner, and a comparator. The image detector, which detects a radiographic image of an object, includes a plurality of pixels arranged in an image capturing field. Each of the pixels receives the radiation emitted from the radiation source, and outputs a pixel value in accordance with an applied radiation dose. The pixel determiner determines at least one typical low-value pixel from the pixels based on the pixel values, and sets the typical low-value as an exposure control pixel. The comparator compares a first integrated value being an integrated value of the pixel value of the typical low-value pixel with a predetermined first threshold value, and performs radiation emission control such that, when the first integrated value has reached the first threshold value, the radiation source stops emitting the radiation.

A control method of a radiation imaging apparatus includes the steps of determining at least one typical low-value pixel from pixels based on pixel values, and setting the typical low-value pixel as an exposure control pixel; and comparing a first integrated value being an integrated value of the pixel value of the typical low-value pixel with a predetermined first threshold value, and performing radiation emission control such that, when the first integrated value has reached the first threshold value, a radiation source stops emitting radiation.

According to the present invention, exposure control is carried out based on the pixel value of the pixel in the image capturing field of the image detector. Thus, it is possible to simplify the structure of the radiation imaging apparatus. Furthermore, at least one typical low-value pixel is determined out of the pixels of the image capturing field, and the exposure control is performed based on the pixel value of the typical low-value pixel. Therefore, it is possible to obtain the radiographic image having favorable image quality, irrespective of the body portion to be image.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 8 is an explanatory view showing an example of disposition of the short pixels;

DESCRIPTION OF THE PREFERRED EMBODIMENTS

Figure 1:
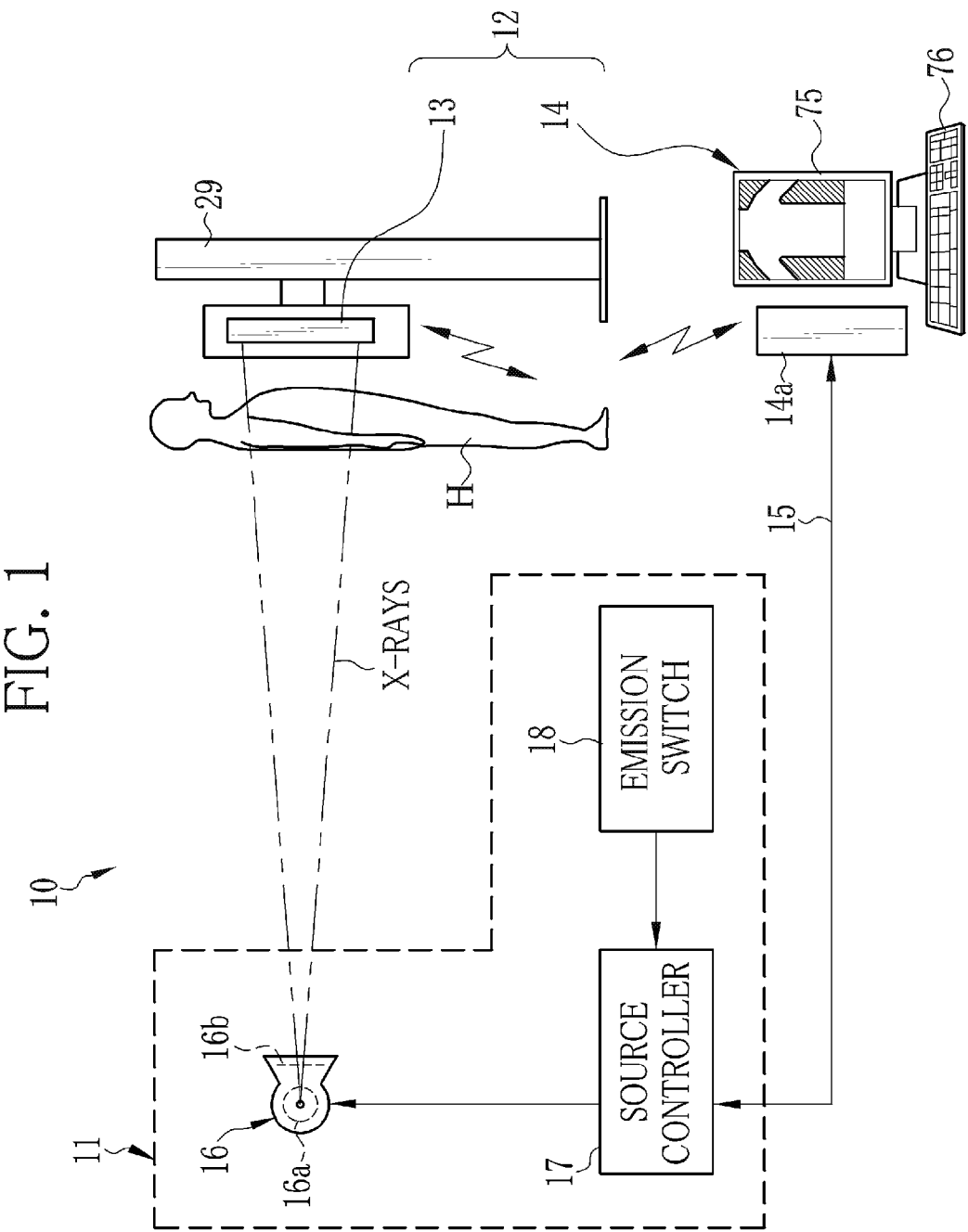
FIG. 1 is an explanatory view showing the schematic structure of an X-ray imaging system.

As shown in FIG. 1, an X-ray imaging system 10 is constituted of an X-ray generating apparatus 11 for generating X-rays and an X-ray imaging apparatus 12 for taking an X-ray image from the X-rays passed through a body portion (object) of a patient H. The X-ray imaging apparatus 12 includes an electronic cassette 13 for detecting the X-ray image and a console 14 that controls the electronic cassette 13 and performs image processing of the X-ray image. In the X-ray imaging system 10, the console 14 is communicatably connected to the X-ray generating apparatus 11 (concretely, a source controller 17) through a cable 15. The electronic cassette 13 and the console 14 are wirelessly communicatable with each other. The X-ray imaging system 10 carries out AEC (automatic exposure control) in which the console 14 stops X-ray emission from the X-ray generating apparatus 11 at the instant when an X-ray dose detected by the electronic cassette 13 has reached a predetermined value.

The X-ray generating apparatus 11 is constituted of an X-ray source 16, the source controller 17 for controlling the X-ray source 16, and an emission switch 18 for commanding the start of X-ray emission. The X-ray source 16 has an X-ray tube 16a for emitting the X-rays and a collimator 16b for limiting an irradiation field of the X-rays emitted from the X-ray tube 16a. The X-ray tube 16a has a cathode being a filament for emitting thermoelectrons and an anode (target) that radiates the X-rays by collision of the thermoelectrons emitted from the cathode. The collimator 16b is composed of, for example, four X-ray shielding lead plates disposed on each side of a rectangle so as to form an irradiation opening in its middle through which the X-rays propagate. A parallel shift of the lead plates varies the size of the irradiation opening to limit the irradiation field.

The electronic cassette 13 is detachably loaded in a holder of an imaging stand 29 or an imaging table (not shown) in such a position that an image capturing field 41 (see FIG. 4) of an FPD (image detector) 26 is opposed to the X-ray source 16. The imaging stand 29 or the imaging table may be designed specific to the electronic cassette 13, or sharable with a film cassette and an IP cassette. The electronic cassette 13 may be used by itself with being put on a bed under the patient H lying, or held by the patient H himself/herself.

Figure 2:
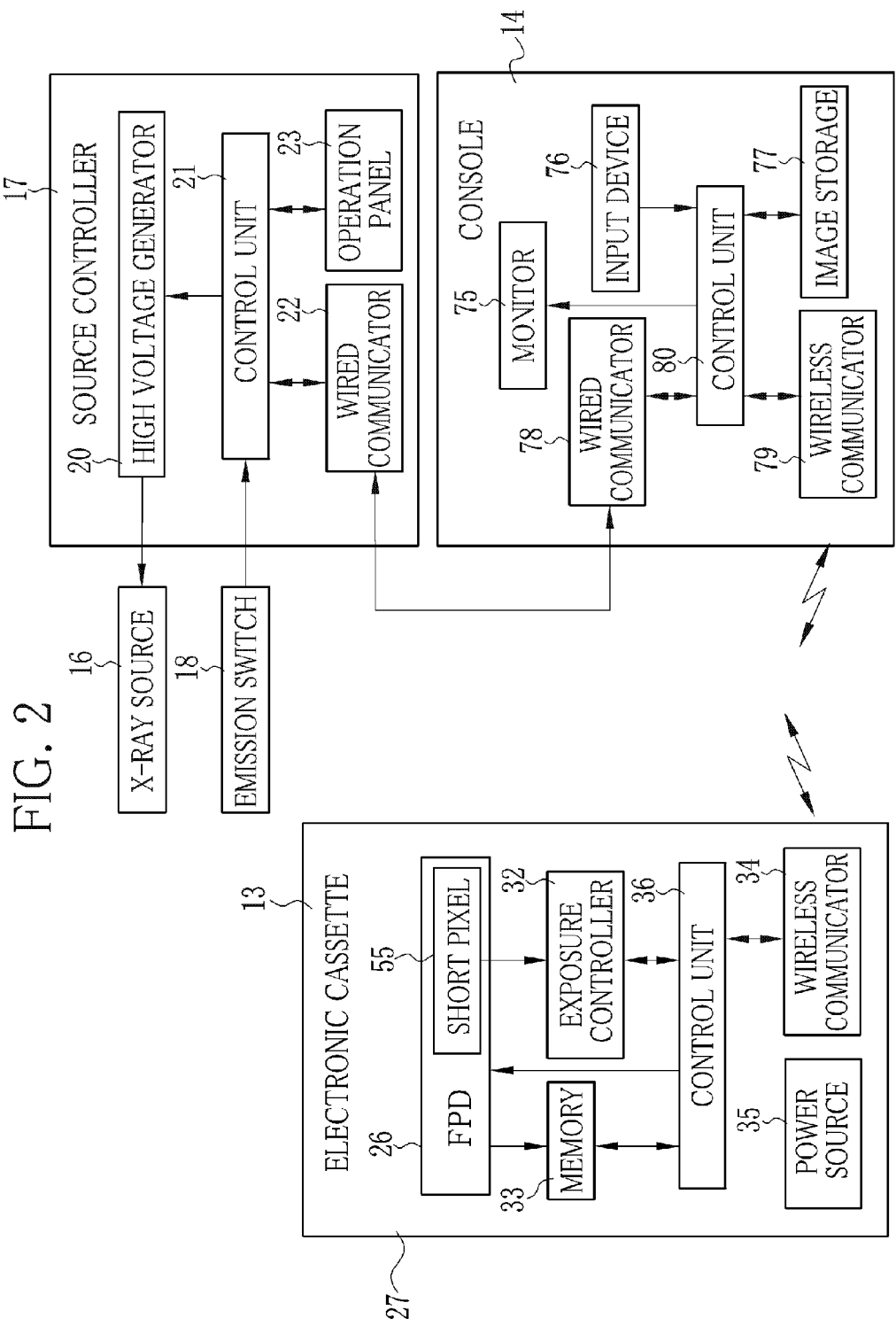
FIG. 2 is a block diagram of the X-ray imaging system.

As shown in FIG. 2, the source controller 17 includes a high voltage generator 20, a control unit 21, and a wired communicator 22. The high voltage generator 20 supplies high tube voltage to the X-ray source 16. The control unit 21 controls the tube voltage, tube current, irradiation time, and the like. The wired communicator 22 establishes communication with the console 14. The tube voltage determines radiation quality (energy spectrum) of the X-rays emitted from the X-ray source 16. The tube current determines the X-ray dose per unit of time. The high voltage generator 20 converts input voltage into the high voltage by a transformer, and supplies drive power to the X-ray source 16 through a high voltage cable.

An imaging condition including the tube voltage, the tube current, the irradiation time, and the like is inputted from the console 14 to the control unit 21 through the wired communicator 22. The control unit 21 sets up a drive condition of the X-ray source 16 based on the imaging condition. The imaging condition may be inputted from an operation panel 23 provided in the source controller 17.

The emission switch 18 connected to the control unit 21 of the source controller 17 through a signal cable is operated by a radiological technician. The emission switch 18 is a two-step press switch, for example. Upon a half press of the emission switch 18, a warm-up start signal is issued to start warming up the X-ray source 16. Upon a full press, an emission start signal is issued to start the X-ray emission from the X-ray source 16. The warm-up start signal and the emission start signal issued from the emission switch 18 are inputted to the control unit 21 through the signal cable.

While the emission switch 18 is fully pressed, the X-ray source 16 is allowed to emit the X-rays. If the full press of the emission switch 18 is released before performing AEC, the X-ray emission is stopped. Thus, it is possible to immediately stop the X-ray emission in case of emergency.

Upon receiving the emission start signal from the emission switch 18, the control unit 21 of the source controller 17 issues an emission start command to the X-ray source 16, and makes the high voltage generator 20 start electric power supply for the X-ray emission. Upon transmission of the emission stop signal from the electronic cassette 13 through the console 14 to the source controller 17 by AEC, the control unit 21 issues an emission stop command to the X-ray source 16, and makes the high voltage generator 20 stop the electric power supply.

The electronic cassette 13 includes the FPD 26, an exposure controller 32, a memory 33, a wireless communicator 34, a power source 35, and a control unit 36. The FPD 26 detects an X-ray image based on the X-rays applied to its irradiation surface 25 through the object. The exposure controller 32 performs AEC. The memory 33 stores image data outputted from the FPD 26. The wireless communicator 34 establishes communication with the console 14. The power source 35 supplies electric power from a battery to each part of the electronic cassette 13. The control unit 36 controls the entire operation of the electronic cassette 13. The components described above are contained in a portable housing 27.

Figure 3:
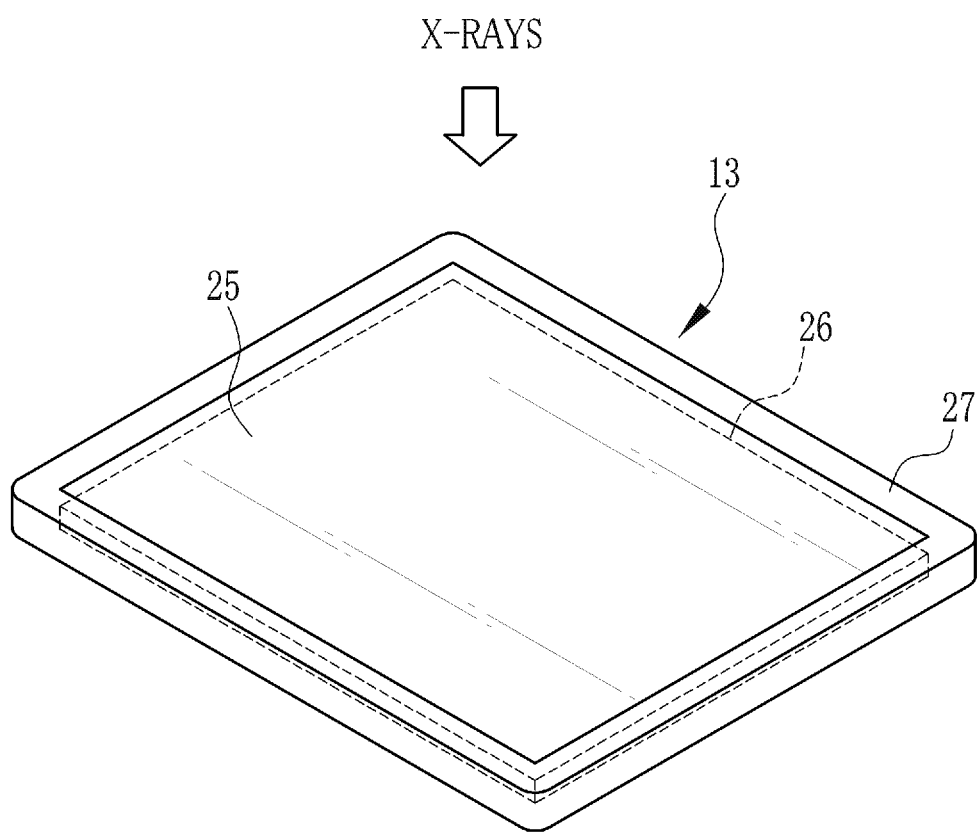
FIG. 3 is a perspective view of an electronic cassette.

As shown in FIG. 3, the housing 27 is in the shape of a rectangular flat box approximately the same size as the film cassette and the IP cassette. The housing 27 is provided with the battery for supplying the electric power to the electronic cassette 13 on a surface opposite to the irradiation surface 25.

The console 14 includes a monitor 75, an input device 76, and a main body 14a. The monitor 75 displays an examination order, the X-ray image, and the like. The input device 76 is used for input of the imaging condition and the like. The main body 14a is constituted of an image storage 77 for storing the X-ray image data, a wired communicator 78 for establishing communication with the source controller 17, a wireless communicator 79 for establishing communication with the electronic cassette 13, and a control unit 80 for controlling the entire operation of the console 14.

The control unit 80 of the console 14 receives input of the examination order including information about the sex and age of the patient, a body portion to be imaged, an examination purpose, and the like, and displays the examination order on the monitor 75. The examination order is inputted from an external system that manages patient data or examination data related to radiography such as a HIS (hospital information system) or a RIS (radiography information system) connected through the wired communicator 78 or the wireless communicator 79, or inputted manually by the radiological technician with the input device 76. The radiological technician inputs the imaging condition, which includes the tube voltage, the tube current, the irradiation time, from the input device 76 to the control unit 80 based on the contents of the examination order displayed on the monitor 75.

The control unit 80 transmits the imaging condition to the electronic cassette 13 and the source controller 17, and sets up in the electronic cassette 13 a signal processing condition of the FPD 26 including first and second threshold values and the like. The control unit 80 receives the image data from the electronic cassette 13, and applies to the image data various types of image processing such as gamma correction and frequency processing. The X-ray image after the image processing is displayed on the monitor 75 of the console 14. Also, the X-ray image data is written to the image storage 77 composed of a hard disk drive or the like, and/or a data storage device such as an image storage server connected to the console 14 through a network.

Figure 4:
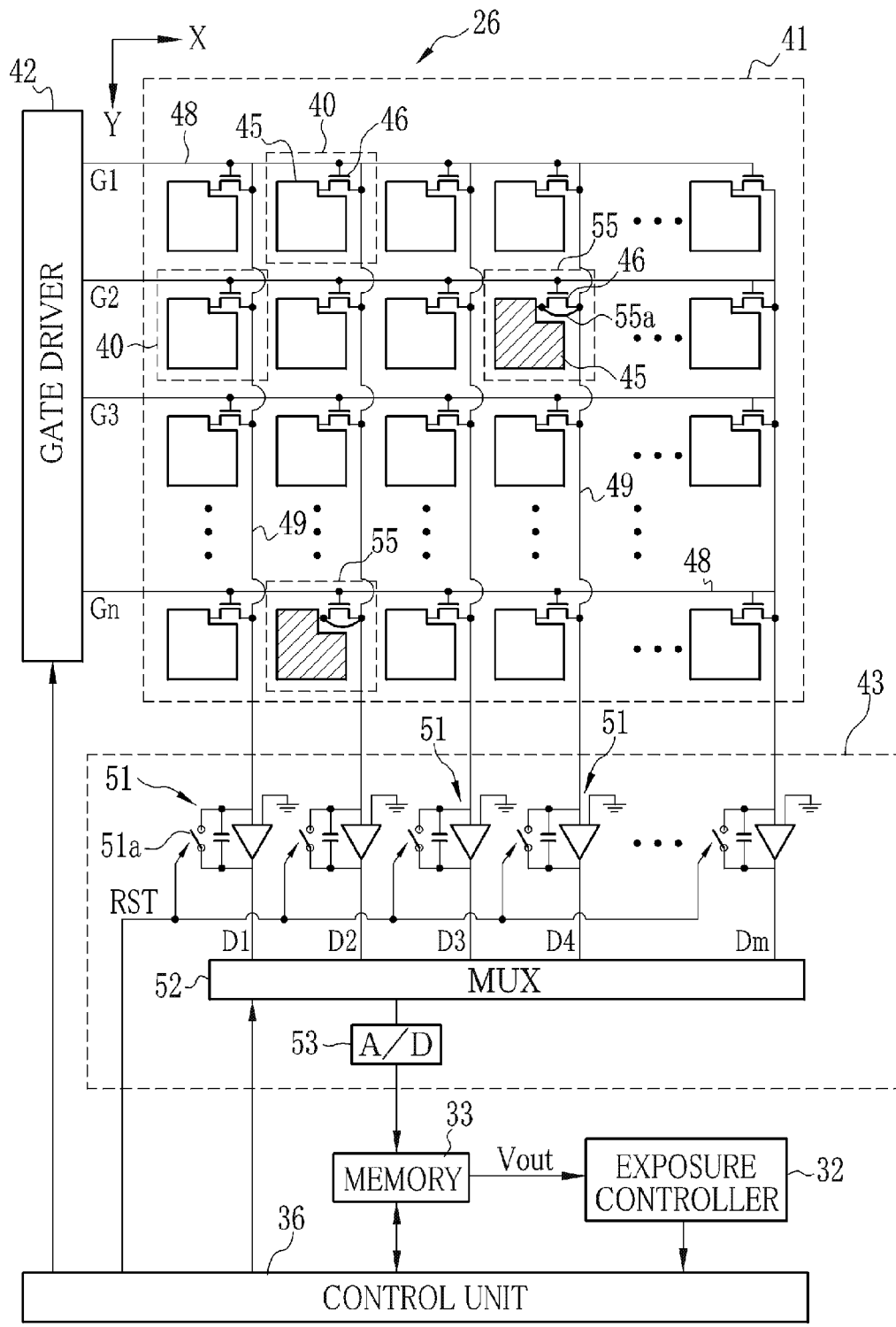
FIG. 4 is a block diagram showing the structure of an FPD.

As shown in FIG. 4, the FPD 26 has a TFT active matrix substrate, and is formed with the image capturing field 41 that is composed of a plurality of pixels (normal pixels 40 and short pixels 55) arranged in the TFT active matrix substrate. Each pixel produces signal charge in accordance with an X-ray dose incident thereon. The plurality of pixels are arranged into a two-dimensional matrix with n rows (Y direction) and m columns (X direction) at a predetermined pitch. The FPD 26 also includes a gate driver 42 and a signal processing circuit 43. The gate driver 42 drives the normal pixels 40 to control readout of the signal charge. The signal processing circuit 43 converts the signal charge readout from the normal pixels 40 into digital image data. The gate driver 42 and the signal processing circuit 43 are controlled by the control unit 36.

The FPD 26 is of an indirect conversion type, which has a scintillator (not shown) for converting the X-rays into visible light. The pixels perform photoelectric conversion of the visible light produced by the scintillator. The scintillator is disposed in front of the image capturing field 41 so as to be opposed to the entire image capturing field 41 having an arrangement of the pixels. The scintillator is made of phosphor such as CsI (cesium iodide) or GOS (gadolinium oxysulfide). Note that, a direct conversion type FPD, which has a conversion layer (amorphous selenium or the like) for directly converting the X-rays into electric charge, may be used instead.

The normal pixel 40 includes a photodiode 45, a capacitor (not shown), and a thin film transistor (TFT) 46. The photodiode 45 being a photoelectric conversion element produces electric charge (electron and hole pairs) upon entry of the visible light. The capacitor accumulates the electric charge produced by the photodiode 45. The TFT 46 functions as a switching element.

The photodiode 45 is composed of a semiconducting layer (of a PIN type, for example) of a-Si (amorphous silicon) or the like, and upper and lower electrodes disposed on the top and bottom of the semiconducting layer. The lower electrode of the photodiode 45 is connected to the TFT 46. The upper electrode of the photodiode 45 is connected to a bias line (not shown).

Through the bias line, bias voltage is applied to the upper electrode of the photodiode 45 of every pixel in the image capturing field 41. Since the application of the bias voltage produces an electric field in the semiconducting layer of the photodiode 45, the electric charge (electron and hole pairs) produced in the semiconducting layer by the photoelectric conversion is attracted to the upper and lower electrodes, one of which has positive polarity and the other has negative polarity. Thereby, the electric charge is accumulated in the capacitor.

A gate electrode of the TFT 46 is connected to a scan line 48. A source electrode of the TFT 46 is connected to a signal line 49. A drain electrode of the TFT 46 is connected to the photodiode 45. The scan lines 48 and the signal lines 49 are routed into a lattice. The number of the scan lines 48 coincides with the number of the rows (n rows) of the pixels provided in the image capturing field 41, and all the pixels arranged in the same row are connected to the same scan line 48. The number of the signal lines 49 coincides with the number of the columns (m columns) of the pixels, and all the pixels arranged in the same column are connected to the same signal line 49. Every scan line 48 is connected to the gate driver 42, and every signal line 49 is connected to the signal processing circuit 43.

The gate driver 42 drives the TFTs 46 so that the FPD 26 carries out a charge accumulation operation, a readout operation, and a reset operation. In the charge accumulation operation, the normal pixels 40 accumulate the signal charge by an amount corresponding to the X-ray dose incident thereon during the X-ray emission. In the readout operation, the signal charge is read out from the normal pixels 40 after the X-ray emission. The reset operation is performed immediately before the X-ray emission to discharge and reset the signal charge accumulated in the normal pixels 40. The control unit 36 controls start timing of each operation described above carried out by the gate driver 42.

In the charge accumulation operation, every TFT 46 is turned off, so every normal pixel 40 accumulates the signal charge. In the readout operation, the gate driver 42 sequentially issues gate pulses G1 to Gn each of which drives the TFTs 46 of the same row at a time. Thereby, the scan lines 48 are activated one by one so as to turn on the TFTs 46 connected to the activated scan line 48 on a row-by-row basis.

Upon turning on the TFTs 46 of the single row, the signal charge accumulated in the normal pixels 40 of the single row is inputted to the signal processing circuit 43 through the signal lines 49. The signal processing circuit 43 reads out output voltage corresponding to the signal charge as voltage signals D1 to Dm. Each of the analog voltage signals D1 to Dm is converted into a digital pixel value, being a detection value of each pixel, after predetermined gain adjustment. This pixel value is also called QL (quantum level) value. The image data that is composed of the pixel values of the pixels is outputted to the memory 33 contained in the electronic cassette 13.

Dark current occurs in the semiconducting layer of the photodiode 45 irrespective of the presence or absence of entry of the X-rays. Dark charge of the dark current is accumulated in the capacitor due to the application of the bias voltage. The dark charge becomes noise of the image data, and therefore the reset operation is carried out to remove the dark charge. The reset operation is an operation of discharging unnecessary electric charge e.g. the dark charge accumulated in the normal pixels 40 through the signal lines 49.

The reset operation adopts a sequential reset method, for example, by which the pixels are reset on a row-by-row basis. In the sequential reset method, as in the case of the readout operation of the signal charge, the gate driver 42 sequentially issues the gate pulses G1 to Gn to the scan lines 48 to turn on the TFTs 46 of the pixels on a row-by-row basis. While the TFT 46 is turned on, the dark charge flows from the pixel through the signal line 49 into the signal processing circuit 43. In the reset operation, in contrast to the readout operation, output voltage corresponding to the dark charge is not read out. In synchronization with the issue of each of the gate pulses G1 to Gn, the control unit 36 outputs a reset pulse RST to the signal processing circuit 43. In the signal processing circuit 43, the input of the reset pulse RST turns on reset switches 51a of integration amplifiers 51 described later on, so the integration amplifiers 51 are reset.

Instead of the sequential reset method, a parallel reset method or an all pixels reset method may be used. In the parallel reset method, a plurality of rows of the pixels are grouped together, and sequential reset is carried out in each group, so as to concurrently discharge the dark charge from the rows of the number of the groups. In the all pixels reset method, the gate pulse is inputted to every row to concurrently discharge the dark charge from every pixel. Adoption of the parallel reset method and the all pixels reset method can reduce time required for the reset operation.

The signal processing circuit 43 is provided with the integration amplifiers 51, a MUX 52, an A/D converter 53, and the like. One integration amplifier 51 is connected to each signal line 49. The integration amplifier 51 includes an operational amplifier and a capacitor connected between input and output terminals of the operational amplifier. The signal line 49 is connected to one of two input terminals of the operational amplifier. The other input terminal of the operational amplifier is connected to a ground (GND). The integration amplifiers 51 integrate the signal charge inputted from the signal lines 49, and convert the signal charge into the voltage signals D1 to Dm, and output the voltage signals D1 to Dm.

In the readout operation for reading out the signal charge from every normal pixel 40 after the charge accumulation operation, the TFTs 46 are turned on from row to row by the gate pulses. The signal charge flows from the capacitors of the normal pixels 40 in the activated row into the integration amplifiers 51 through the signal lines 49.

An output terminal of the integration amplifier 51 of every column is connected to the MUX 52 through another amplifier (not shown) for amplifying each of the voltage signals D1 to Dm and a sample holder (not shown) for holding each of the voltage signals D1 to Dm. The MUX 52 sequentially chooses one of the plurality of integration amplifiers 51 connected in parallel, in order to input the voltage signals D1 to Dm in series from the chosen integration amplifier 51 to the A/D converter 53.

The A/D converter 53 converts the analog voltage signals D1 to Dm into the digital pixel values in accordance with their signal levels, and outputs the pixel values to the memory 33. The pixel values are stored in the memory 33 as the X-ray image data representing the X-ray image with being associated with the coordinates of each normal pixel 40 in the image capturing field 41.

After the voltage signals D1 to Dm of one row are outputted from the integration amplifiers 51, the control unit 36 issues the reset pulse RST to the integration amplifiers 51 to turn on the reset switches 51a of the integration amplifiers 51. Thus, the signal charge of the single row that is accumulated in the integration amplifiers 51 is reset. After the reset of the integration amplifiers 51, the gate driver 42 outputs the gate pulse of the next row, so the signal charge is read out from the normal pixels 40 of the next row. The above operation is repeated in sequence to read out the signal charge from the normal pixels 40 of every row.

After completion of the readout from every row, the image data representing the X-ray image of one frame is written to the memory 33. The control unit 36 applies image correction processing including offset correction, sensitivity correction, and defect correction to this image data. In the offset correction, an offset component being fixed pattern noise caused by the individual difference and the environment of the FPD 26 is eliminated. In the sensitivity correction, variations in sensitivity among the photodiodes 45, variations in output property of the signal processing circuit 43, and the like are corrected. In the defect correction, the pixel value of a defect pixel is linearly interpolated using the pixel value of the normal pixel 40 adjoining to the defect pixel, based on defect pixel information produced in shipment or periodic inspection. The pixel value of the short pixel 55 used in AEC, as described later on, is also subjected to the defect correction. The image data is read out from the memory 33, and is transmitted to the console 14 through the wireless communicator 34.

The FPD 26 is provided with not only the normal pixels 40 for specific use in detection of the X-ray image but also the plurality of short pixels 55, which are hatched in FIG. 4, in its image capturing field 41. The short pixel 55 is a detection pixel that detects an X-ray dose applied to the FPD 26 through the object. The short pixels 55 are used in AEC performed by the exposure controller 32 and obtainment of operation switching timing of the FPD 26.

The short pixels 55 are distributed evenly across the entire image capturing field 41 without being localized. The short pixels 55 occupy, for example, about 0.01% of the all pixels including the normal pixels 40 and the short pixels 55 in the image capturing field 41. The positions of the short pixels 55 are known in manufacturing the FPD 26. The FPD 26 has a nonvolatile memory (not shown) that stores the position (coordinates) of every short pixel 55. The layout, number, and rate of the short pixels 55 are appropriately changeable.

Each short pixel 55 has the photodiode 45 and the TFT 46, as with the normal pixel 40. The photodiode 45 of the short pixel 55 produces the signal charge in accordance with the X-ray dose incident thereon. The difference in the structure between the short pixel 55 and the normal pixel 40 is that the short pixel 55 has a connection 55a that brings a short between the source and the drain of the TFT 46, and hence the short pixel 55 has no switching function of the TFT 46. Thus, the signal charge produced in the photodiode 45 of the short pixel 55 continuously flows out through the signal line 49 into the integration amplifier 51. Note that, instead of connecting the source and the drain of the TFT 46 of the short pixel 55, the short pixel 55 may not be provided with the TFT 46 and the photodiode 45 may be directly connected to the signal line 49.

The signal charge from the short pixels 55 that has been inputted to the integration amplifiers 51 is outputted to the A/D converter 53, as with the signal charge from the normal pixels 40. The A/D converter 53 converts the signal charge into digital pixel values Vout, and outputs the pixel values Vout to the memory 33. The pixel values Vout of the short pixels 55 are stored in the memory 33 with being associated with the coordinates of each short pixel 55. Thus, the X-ray dose that has been applied to each short pixel 55 is detected. The FPD 26 repeats this sampling operation of the pixel values Vout of the short pixels 55 at a predetermined rate during the X-ray emission. The exposure controller 32 reads out the sampled pixel values Vout of the short pixels 55 from the memory 33 to carry out AEC.

Figure 5:
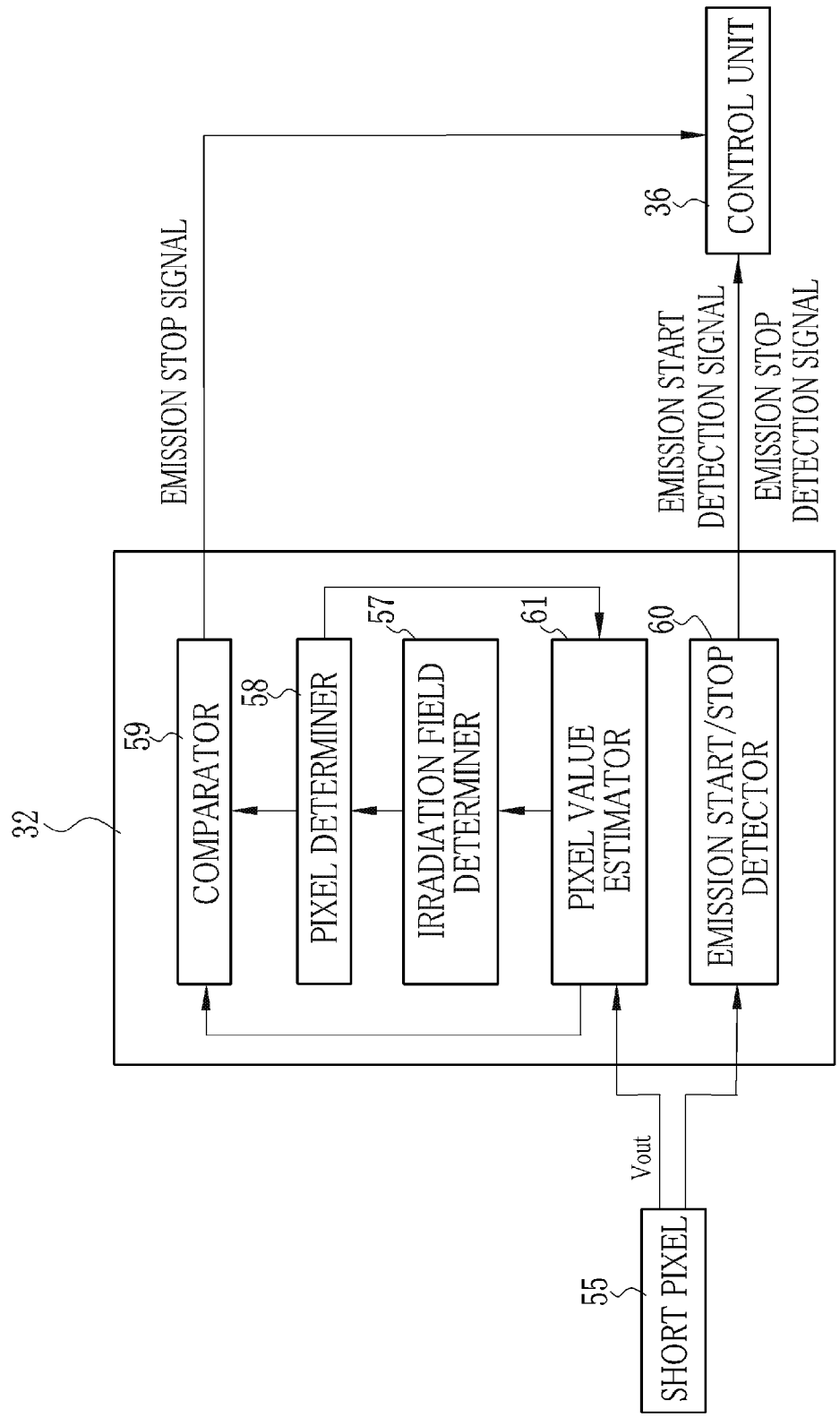
FIG. 5 is a block diagram showing the structure of an exposure controller.

As shown in FIG. 5, the exposure controller 32 is provided with an irradiation field determiner 57, a pixel determiner 58, a comparator 59, and an emission start/stop detector 60. The irradiation field determiner 57, which determines the irradiation field of the X-rays applied from the X-ray source 16 in AEC, is composed of the short pixels 55 described above and a pixel value estimator 61. An irradiation field determination process by the irradiation field determiner 57 will be hereinafter described with referring to FIGS. 6 to 10B.

Figure 7:
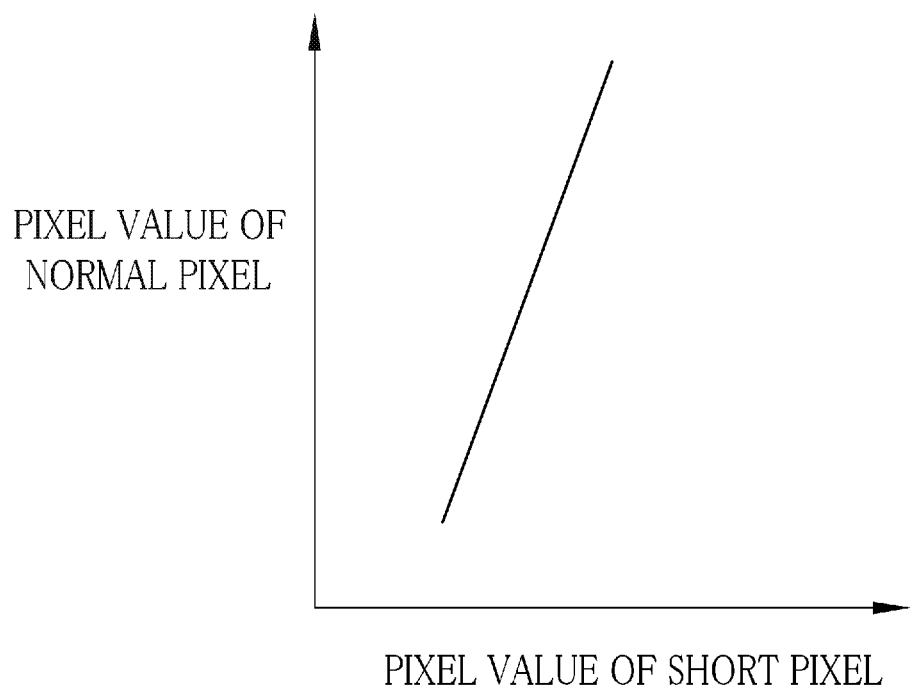
FIG. 7 is a graph showing the correlation between a pixel value of a normal pixel and a pixel value of a short pixel.

The pixel value estimator 61 estimates the pixel value of the normal pixel 40 based on the pixel value Vout of the short pixel 55 positioned in the vicinity of the normal pixel 40 (S10). As shown in FIG. 7, due to the positive correlation between the pixel value of the normal pixel 40 and the pixel value Vout of the short pixel 55 positioned in the vicinity thereof, the pixel value of the normal pixel 40 can be estimated from the pixel value Vout of the short pixel 55 with high accuracy. Note that, the pixel value of the normal pixel 40 and the pixel value Vout of the short pixel 55 have a linear correlation in FIG. 7, but may have a nonlinear correlation depending on the structure and positions of the pixels.

The pixel value estimator 61 may estimate the pixel value of the normal pixel 40 based on the pixel value Vout of the short pixel 55 obtained by single sampling, or based on an integrated value of the pixel values Vout, which are sampled two or more times from the single short pixel 55 and integrated from one coordinate to another.

In this embodiment, to improve accuracy in the estimation of the pixel value of the normal pixel 40, a plurality of pixel groups each of which has a fixed number of pixels in row and column directions are established in the FPD 26. Each pixel group includes a predetermined number of normal pixels 40 and a predetermined number of short pixels 55. The positions of the short pixels 55 differ between the pixel groups adjoining in the column direction, for example. In an example shown in FIG. 8, first to sixth pixel groups 63 to 68, each including 3 by 3 pixels in the row and column directions (X and Y directions), are established. In the first pixel group 63, the three short pixels 55 are arranged in a left column. In the second pixel group 64 adjoining to the first pixel group 63 in the column direction, the three short pixels 55 are arranged in a middle column. In the third pixel group 65 adjoining to the second pixel group 64 in the column direction, the three short pixels 55 are arranged in a right column.

Taking a case of estimating the pixel values of the normal pixels 40 arranged in a middle column of the first pixel group 63 as an example, the pixel value estimator 61 estimates the pixel values based on the pixel values of the short pixels 55 belonging to the same first pixel group 63 and the pixel values of the short pixels 55 belonging to the second pixel group 64. The pixel values of the normal pixels 40 arranged in a right column of the first pixel group 63 are estimated based on the pixel values of the short pixels 55 belonging to the same first pixel group 63 and the pixel values of the short pixels 55 belonging to the third pixel group 65. In a like manner, the pixel value of each of the normal pixels 40 of the second to sixth pixel groups 64 to 68 is estimated from the pixel values of the short pixels 55 belonging to the same pixel group and the pixel values of the short pixels 55 belonging to the near pixel group.

Note that, the pixel value of the normal pixel 40 may be estimated only from the pixel values of the short pixels 55 belonging to the same pixel group, without using the pixel values of the short pixels 55 belonging to the different pixel group. In this case, estimation processing becomes easier, though its accuracy possibly decreases.

Figure 9A:
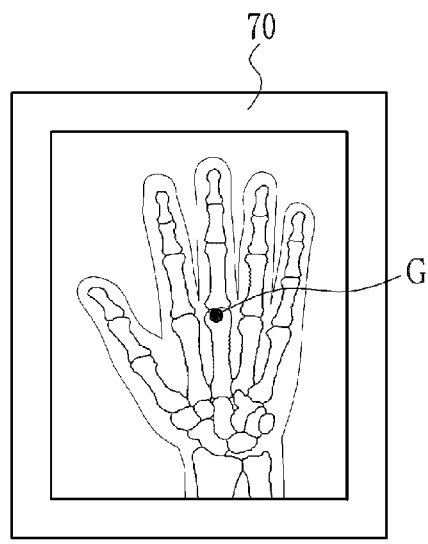
FIGS. 9A to 9D are explanatory views of the irradiation field determination process.

The irradiation field determiner 57 differentiates an image that is composed of the estimated pixel values of the normal pixels 40 to produce a differential image, and obtains a barycenter of differential values from the differential image (S11). In an example shown in FIGS. 9A to 9D, the irradiation field is determined from an image of a right hand of the patient. As shown in FIG. 9A, the irradiation field determiner 57 produces a differential image 70 by differentiation of the image composed of the estimated pixel values of the normal pixels 40, and obtains a barycenter G from the differential image 70.

Figure 9B:
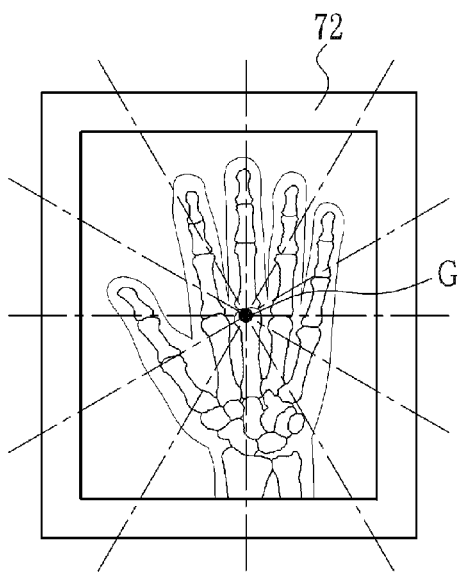
Figure 10A:
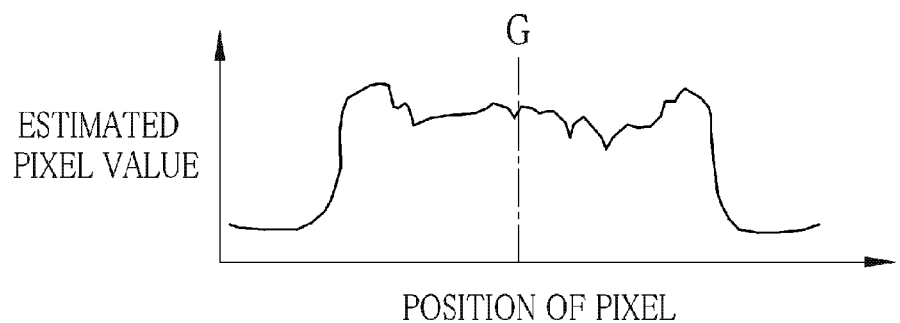
FIGS. 10A and 10B are graphs showing an example of profiles that are produced to obtain edges of the irradiation field.
Figure 10B:
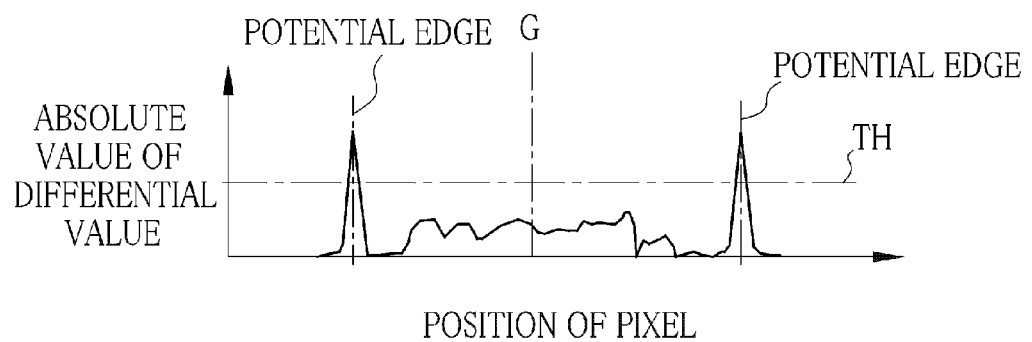

Next, potential points of the edge of the irradiation field are extracted (S12). As shown in FIG. 9B, the irradiation field determiner 57 performs differential processing of an image 72, which is composed of the estimated pixel values of the normal pixels 40, with respect to a plurality of directions radiating from the barycenter G. To be more specific, as shown in FIG. 10A, a profile of the pixel values of the image 72 is produced in each radiating direction, and this profile is subjected to the differential processing to create a profile of absolute values of the differential values, as shown in FIG. 10B. Then, the absolute differential values are compared with a predetermined threshold value TH. The coordinates of the pixel that has the absolute differential value larger than the threshold value TH are extracted as the potential point of the edge of the irradiation field.

Six radiating directions thirty degrees apart from each other are set in FIG. 9B, but the number of the radiating directions is preferably increased. In the above embodiment, the profile is produced in the plurality of directions radiating from the barycenter G of the differential image 72. However, if it is conceivable that the rectangular irradiation field is not rotated or skewed with respect to the image, an easier method is adoptable in which the profile may be detected in two directions, that is, vertical and horizontal directions. Note that, other irradiation field determination methods are known in Japanese Patent No. 2525652, Japanese Patent Laid-Open Publication Nos. 63-259538 and 10-162156, and the like. The methods described in the art may be adopted instead.

Figure 9C:
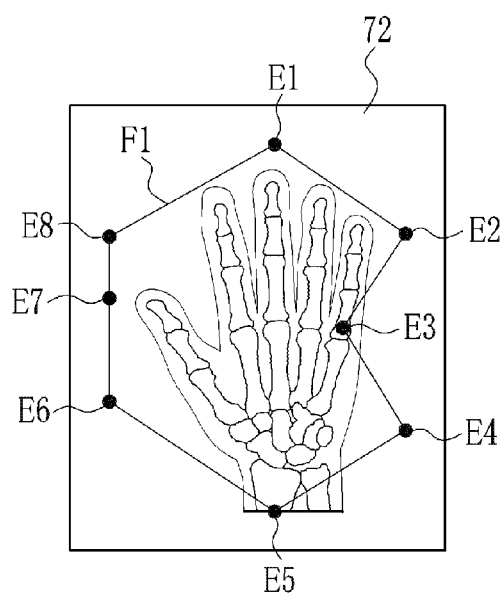
Figure 9D:
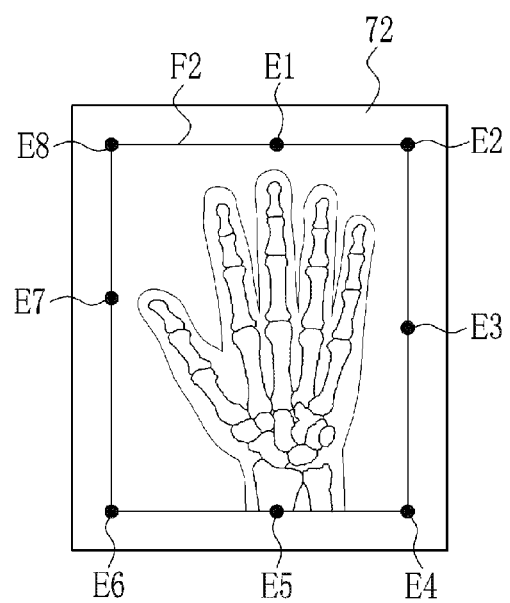

Next, several edge points are determined from the extracted potential points (S13). To be more specific, for example, the irradiation field determiner 57 re-evaluates whether or not each midpoint between the potential points next to each other is actually in the edge of the irradiation field, and determines eight edge points E1 to E8, as shown in FIG. 9C. In the next step, the irradiation field is determined from the edge points E1 to E8 (S14). As shown in FIG. 9C, the irradiation field determiner 57 creates a polygonal field F1 by connecting the determined eight edge points E1 to E8 by straight lines. Then, as shown in FIG. 9D, the irradiation field determiner 57 corrects the position of the edge point E3 that is unnaturally recessed, and corrects the shape of the field F1 in accordance with the shape of the irradiation field defined by the collimator 16b to determine a rectangular irradiation field F2.

The pixel determiner 58 determines pixels to be used in AEC, out of the normal pixels 40 located within the irradiation field F2 determined by the irradiation field determiner 57. Based on the pixel values of the normal pixels 40 estimated by the pixel value estimator 61, the pixel determiner 58 determines a minimum-value pixel whose pixel value is the lowest and a maximum-value pixel whose pixel value is the highest. The minimum-value pixel and the maximum-value pixel are used in AEC. The minimum-value pixel is set as a typical low-value pixel that is used for obtaining the X-ray image with favorable image quality. The maximum-value pixel is set as a typical high-value pixel that is used for preventing excessive X-ray exposure of the patient.

Figure 11:
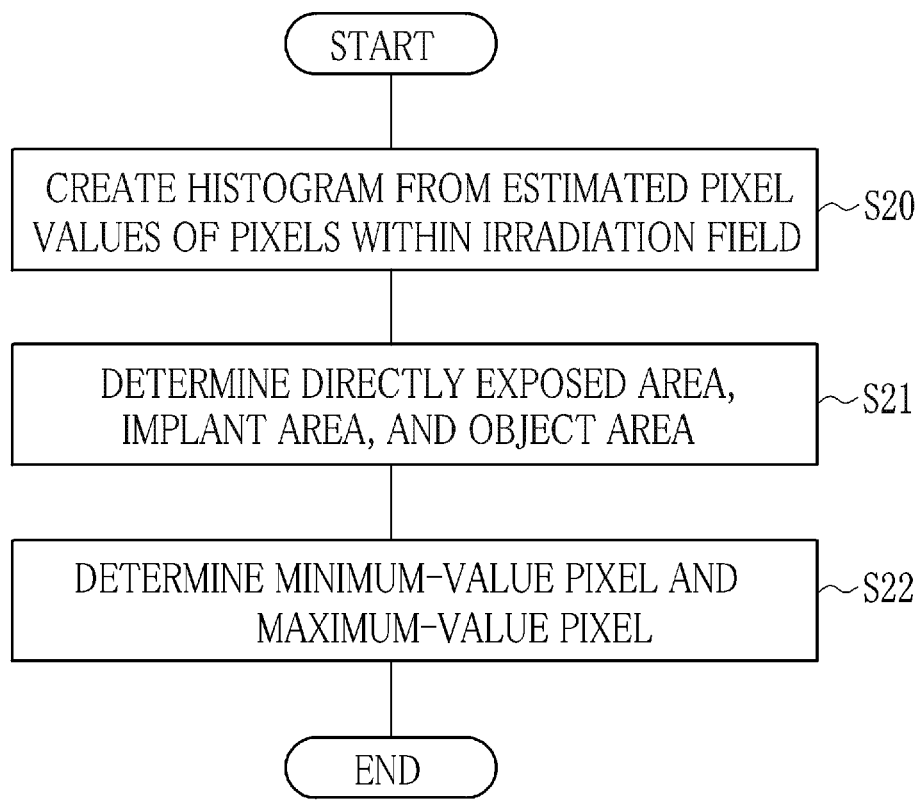
FIG. 11 is a flowchart of a process of setting a minimum-value pixel and a maximum-value pixel.
Figure 12:
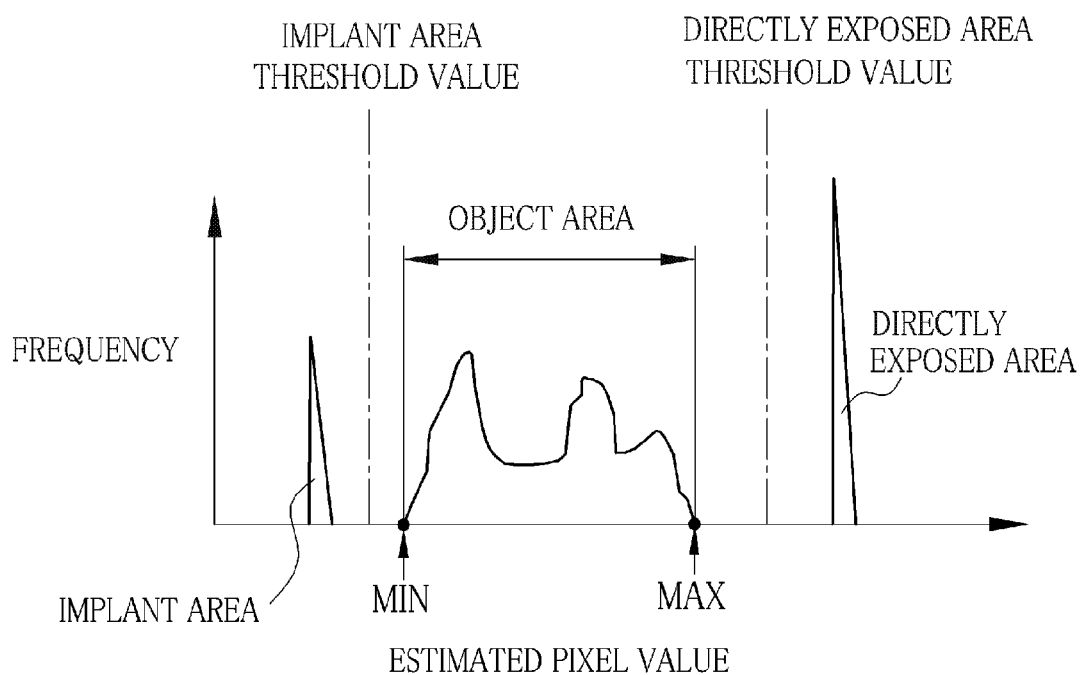
FIG. 12 is a graph showing an example of a histogram that is produced to determine an object area.

Referring to FIG. 11, a setting process of the minimum-value pixel and the maximum-value pixel by the pixel determiner 58 will be described. As shown in FIG. 12, the pixel determiner 58 creates a histogram of the estimated pixel values of the normal pixels 40 located within the irradiation field F2 (S20). The pixel determiner 58 analyzes the created histogram to obtain the minimum-value pixel and the maximum-value pixel. In the histogram, a horizontal axis represents the amount of the estimated pixel value, and a vertical axis represents the frequency of appearance of each estimated pixel value. Then, the pixel determiner 58 determines from the histogram, a directly exposed area to which the X-rays are directly applied without through the object and an implant area in which an implant is present in the object. The pixel determiner 58 determines an object area by excluding the directly exposed area and the implant area from the irradiation field F2 (S21).

The pixel value is higher in the directly exposed area than in the object area, because the X-rays are not absorbed by the object in the directly exposed area. The pixel determiner 58 detects a maximum peak, which represents the maximum estimated pixel value, out of peaks of the histogram, for example. The pixel value of the maximum peak is multiplied by a certain rate less than one, and the multiplied pixel value is set as a directly exposed area threshold value. In the irradiation field F2, an area having the pixel values that are equal to or more than the directly exposed area threshold value is determined as the directly exposed area. On the other hand, when the object is a living human body, the X-ray absorptance of the implant is higher than that of the object. Thus, the pixel value is lower in the implant area than in the object area. The pixel determiner 58 detects a minimum peak, which represents the minimum estimated pixel value, out of the peaks of the histogram, for example. The pixel value of the minimum peak is multiplied by a certain rate more than one, and the multiplied pixel value is set as an implant area threshold value. In the irradiation field F2, an area having the pixel values that are equal to or less than the implant area threshold value is determined as the implant area. Note than, the rates used for calculation of the directly exposed area threshold value and the implant area threshold value are changeable in accordance with the body portion to be imaged.

The pixel determiner 58 determines based on the histogram a pixel whose estimated pixel value is the lowest (MIN) out of the normal pixels 40 in the object area, and sets this pixel as the minimum-value pixel. In a like manner, the pixel determiner 58 determines a pixel whose estimated pixel value is the highest (MAX), and sets this pixel as the maximum-value pixel (S22).

Figure 13A:
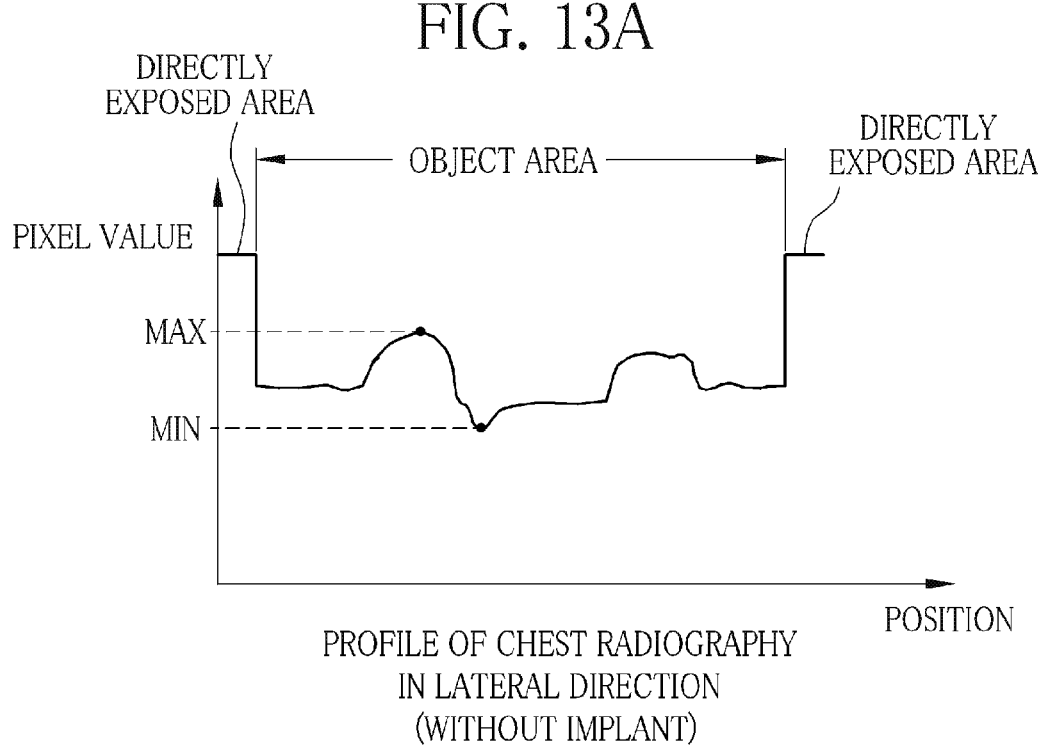
FIG. 13A is a graph showing an example of a profile in the absence of an implant.
Figure 13B:
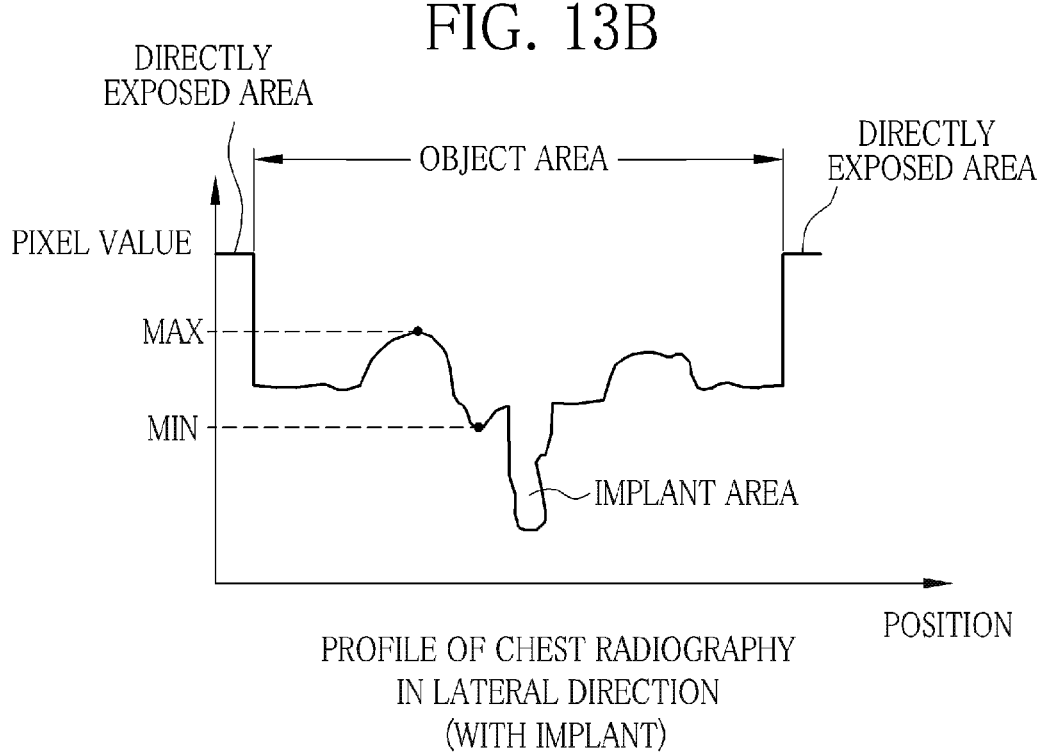
FIG. 13B is a graph showing an example of a profile in the presence of the implant.

The directly exposed area and the implant area are excluded from the irradiation field F2, for the purpose of setting the minimum-value pixel and the maximum-value pixel to be used in AEC within the object area excluding the directly exposed area and the implant area. FIGS. 13A and 13B show profiles of an irradiation field in a lateral direction in chest radiography. FIG. 13A is in the case of the absence of the implant, while FIG. 13B is in the case of the presence of the implant in the middle of the object. In FIGS. 13A and 13B, a horizontal axis represents the horizontal position of the normal pixels 40 in the irradiation field F2, and a vertical axis represents a pixel value. As is known from the profiles, the pixel value is lower in the implant area than in the object area. The pixel value is higher in the directly exposed area than in the object area. Therefore, if the minimum and maximum values are chosen from the pixel values of all the normal pixels 40 located within the irradiation field F2, a pixel within the implant area is set as the minimum-value pixel, and a pixel within the directly exposed area is set as the maximum-value pixel. For this reason, in this embodiment, the object area is determined by excluding the directly exposed area and the implant area from the irradiation field F2, and the minimum-value pixel and the maximum-value pixel are set from the normal pixels 40 within the object area.

In the case of setting the minimum-value pixel and the maximum-value pixel from the one-dimensional profile shown in FIG. 13B, the positions of the minimum value (MIN) and the maximum value (MAX) correspond to the positions of the minimum-value pixel and the maximum-value pixel. Since the object area is a two-dimensional area, there may be cases where the profile of FIG. 13B includes either or neither of the MIN and MAX, as a matter of course.

Figure 14:
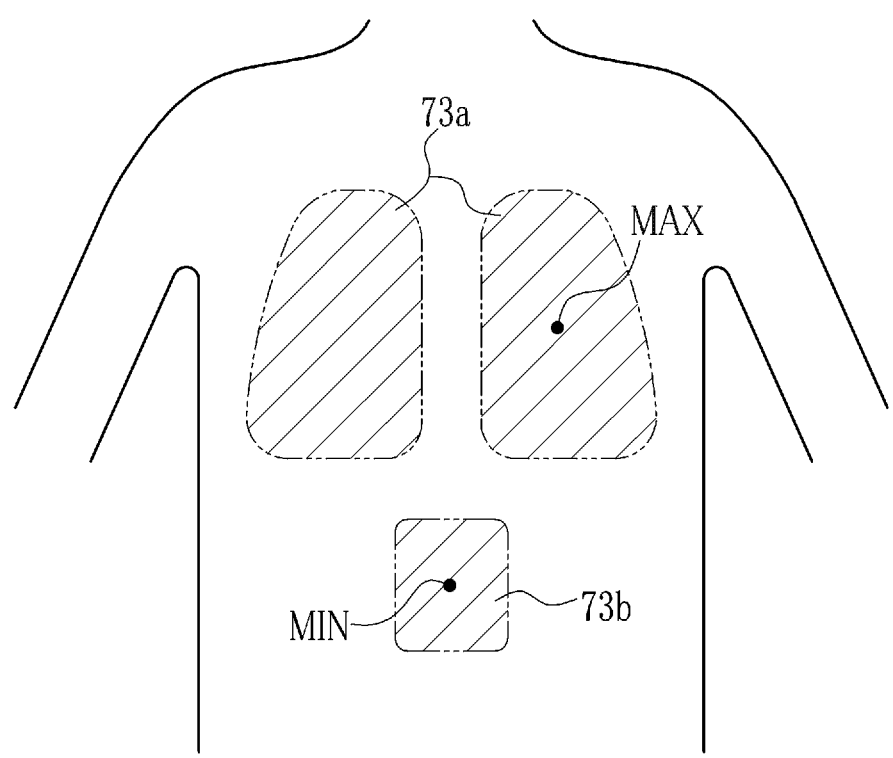
FIG. 14 is an explanatory view showing areas in which the minimum-value pixel and the maximum-value pixel are located.

In the case of the chest radiography, for example, the object area includes right and left lung fields, a mediastinum, a diaphragm, and the like. In the object area, the lung fields have the highest X-ray transmittance, while the mediastinum and the diaphragm have the lowest X-ray transmittance. Therefore, in the chest radiography, as shown in FIG. 14, the minimum-value pixel having the MIN is set in an area 73*b* corresponding to the mediastinum and the diaphragm, while the maximum-value pixel having the MAX is set in areas 73*a* corresponding to the right and left lung fields. The coordinate data of the minimum-value pixel and the maximum-value pixel is inputted to the comparator 59 and the pixel value estimator 61.

The comparator 59 performs AEC based on the estimated pixel values of the minimum-value and maximum-value pixels set by the pixel determiner 58. After the pixel determiner 58 sets the minimum-value and maximum-value pixels, the pixel value estimator estimates the pixel values of the minimum-value and maximum-value pixels, and the estimated pixel values are inputted to the comparator 59 (see FIG. 5). As described above, the pixel values Vout of the short pixels 55 are sampled repeatedly at a predetermined rate. Whenever the sampling is carried out, the pixel value estimator 61 estimates the pixel value of each of the minimum-value and maximum-value pixels based on the pixel values Vout of the short pixels 55, and inputs the estimated pixel values to the comparator 59. The estimated pixel value that is calculated based on the pixel values Vout obtained by the single sampling corresponds to an X-ray dose applied to the minimum-value or maximum-value pixel per unit of time. The comparator 59 integrates the estimated pixel values of the minimum-value pixel inputted in each sampling cycle, to calculate a first integrated value being an integrated value of the estimated pixel values of the minimum-value pixel. The comparator 59 also integrates the estimated pixel values of the maximum-value pixel inputted in each sampling cycle, to calculate a second integrated value being an integrated value of the estimated pixel values of the maximum-value pixel. The first integrated value corresponds to a cumulative amount of the X-ray dose applied to the minimum-value pixel. The second integrated value corresponds to a cumulative amount of the X-ray dose applied to the maximum-value pixel.

Figure 15:
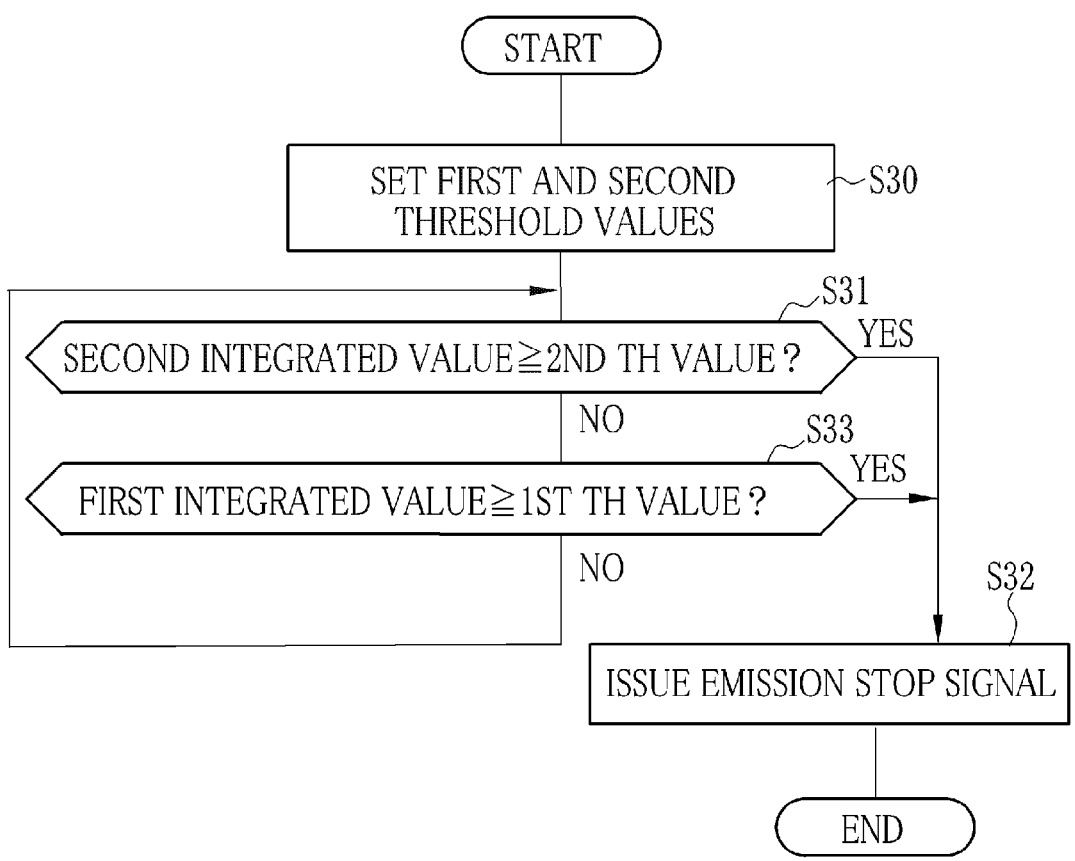
FIG. 15 is a flowchart of an AEC process using first and second integrated values.

As shown in FIG. 15, a first threshold value to be compared with the first integrated value and a second threshold value to be compared with the second integrated value are set in the comparator 59 (S30). The comparator 59 stores a plurality of types of first and second threshold values, which correspond to the body portion to be imaged, in its memory (not shown), and chooses the first and second threshold values based on the body portion included in the imaging condition transmitted from the console 14. The first threshold value represents a necessary dose required for obtaining the favorable image quality of the X-ray image. The second threshold value represents a regulation value to prevent excessive X-ray exposure of the object.

The comparator 59 compares the second integrated value with the second threshold value (S31) to check whether or not the X-ray dose applied to the object has reached the regulation value. In a case where the second integrated value is the second threshold value or more (YES in S31), the comparator 59 judges that the applied X-ray dose has reached the regulation value, and issues an emission stop signal to the control unit 36 of the electronic cassette 13 (S32). The emission stop signal is transmitted from the control unit 36 to the source controller 17 through the console 14. Thereby, the X-ray emission from the X-ray source 16 is stopped.

In a case where the second integrated value is less than the second threshold value (NO in S31), the comparator 59 compares the first integrated value with the first threshold value (S33) to check whether or not the applied X-ray dose has reached the necessary dose. The comparator 59 repeats the comparison between the second integrated value and the second threshold value and between the first integrated value and the first threshold value (S31 and S33), until the first integrated value comes to the first threshold value or more. When the first integrated value is the first threshold value or more (YES in S33), the comparator 59 judges that the applied X-ray dose has reached the necessary dose, and issues the emission stop signal to the control unit 36 of the electronic cassette 13 (S32). As described above, when the second integrated value has reached the second threshold value and the applied X-ray dose has come to the regulation value (YES in S31), the X-ray emission from the X-ray source 16 is stopped, even if the first integrated value is less than the first threshold value.

As described above, AEC is carried out based on the first integrated value of the minimum-value pixel in the object area, so it is possible to obtain the X-ray image with the favorable image quality. The higher the density, the finer the graininess and the higher the image quality of the X-ray image would be. In this embodiment, the minimum-value pixel that is located in a part of the object area having the lowest X-ray transmittance is used as reference of AEC. Thus, the necessary dose is certainly applied not only to the minimum-value pixel but also to the entire object area, so it is possible to obtain the X-ray image having the favorable image quality in the entire object area.

Also, since AEC is carried out based on the second integrated value of the maximum-value pixel in the object area, it is possible to prevent excessive X-ray exposure throughout the object area. For example, if a pixel of the object area having relatively low X-ray transmittance is used as reference, and an integrated value of this reference pixel is compared with the second threshold value (regulation value) for prevention of the excessive X-ray exposure, the X-ray dose could exceed the regulation value in a part having the X-ray transmittance higher than that of the reference pixel. In this embodiment, the maximum-value pixel that is located in a part of the object area having the highest X-ray transmittance is used as reference of AEC. Thus, the applied X-ray dose is the second integrated value or less in the entire object area, so it is possible to prevent the excessive X-ray exposure in the entire object area.

The emission start/stop detector 60 monitors the pixel value Vout of the short pixel 55 during the reset operation of the FPD 26 before the start of X-ray emission. The pixel value Vout of the short pixel 55 is sampled repeatedly at a predetermined sampling rate during the reset operation. Whenever the sampling is performed, the pixel value Vout is inputted to the emission start/stop detector 60. The emission start/stop detector 60 compares the pixel value Vout with a predetermined emission start threshold value. When the pixel value Vout has reached the emission start threshold value, the emission start/stop detector 60 judges that the X-ray source 16 has started the X-ray emission, and issues an emission start detection signal to the control unit 36. Upon receiving the emission start detection signal, the control unit 36 shifts the operation of the FPD 26 from the reset operation to the charge accumulation operation.

The sampling of the pixel value Vout of the short pixel 55 is continued during the X-ray emission. During the X-ray emission, the pixel value Vout is inputted to the emission start/stop detector 60, in addition to being used for AEC, as described above. The emission start/stop detector 60 compares the pixel value Vout of the short pixel 55 with a predetermined emission stop threshold value during the X-ray emission. When the pixel value Vout has reached the emission stop threshold value, the emission start/stop detector 60 judges that the X-ray source 16 has stopped the X-ray emission, and issues an emission stop detection signal to the control unit 36. Upon receiving the emission stop detection signal, the control unit 36 shifts the operation of the FPD 26 from the charge accumulation operation to the readout operation.

Figure 16:
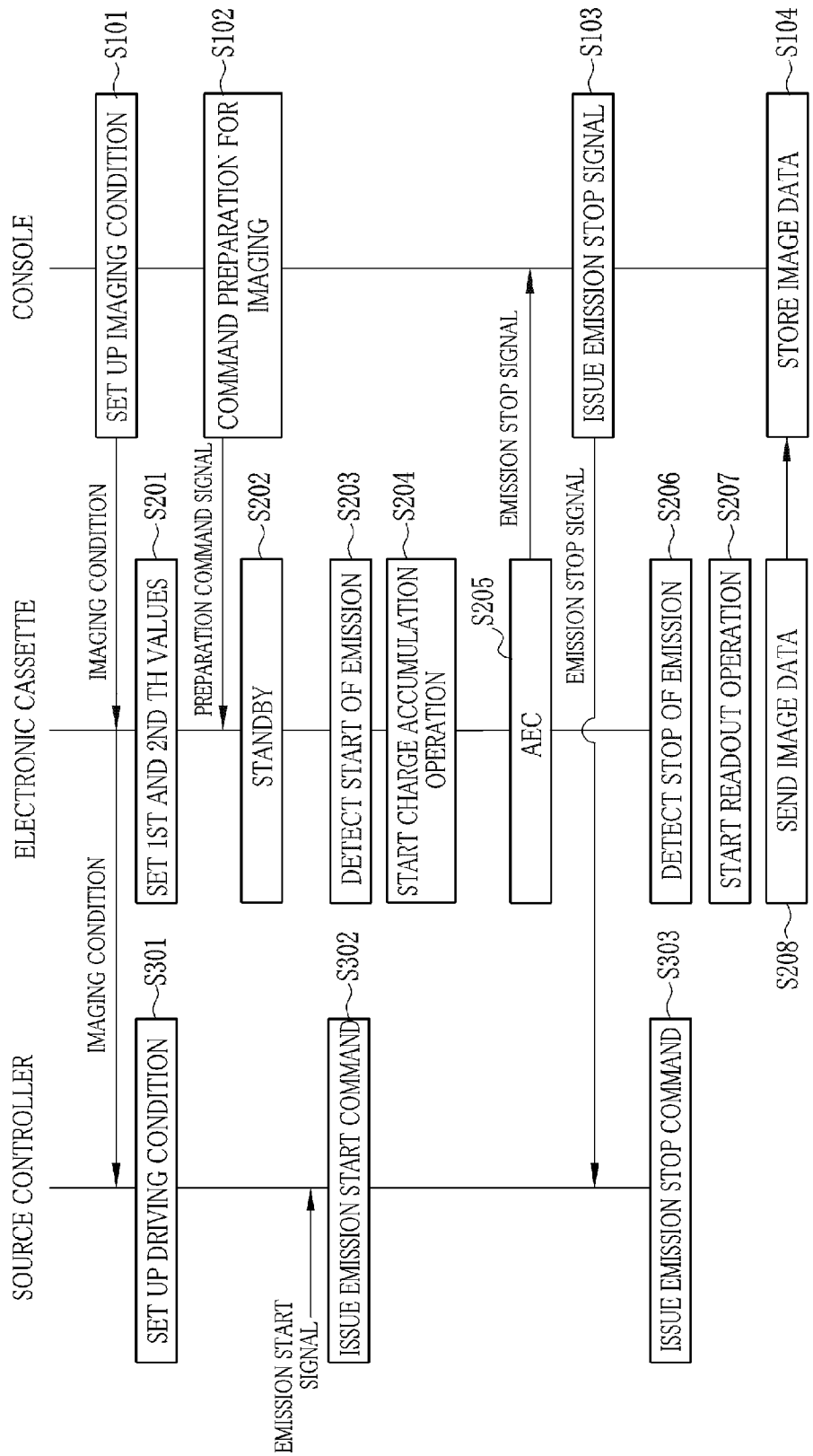
FIG. 16 is a flowchart of an X-ray imaging process of an X-ray imaging system.

Referring to FIG. 16, the operation of the X-ray imaging system 10 will be described. The position adjustment is carried out among the imaging stand 29 loaded with the electronic cassette 13, the body portion of the patient H, and the irradiation position of the X-ray source 16. The examination order including the sex and age of the patient, the body portion to be imaged, the examination purpose, and the like is inputted to the console 14, and the imaging condition is set up based on the examination order (S101). The console 14 transmits the imaging condition to the electronic cassette 13 and the source controller 17.

The control unit 21 of the source controller 17 sets up a driving condition of the X-ray source 16 based on the imaging condition received from the console 14 (S301). The control unit 36 of the electronic cassette 13 sets up the first and second threshold values described above based on the imaging condition received from the console 14 (S201).

The console 14 transmits a preparation command signal, which commands preparation for imaging, to the electronic cassette 13 (S102). Upon receiving the preparation command signal, the electronic cassette 13 shifts the FPD 26 to a standby state (S202). In the standby state, the FPD 26 starts the reset operation, and the emission start/stop detector 60 of the exposure controller 32 begins detecting the start of X-ray emission.

When the emission start signal is inputted from the emission switch 18, the source controller 17 issues the emission start command to the X-ray source 16 (S302). The X-ray source 16 starts applying the X-rays to the object. The emission start/stop detector 60 compares the pixel value Vout of the short pixel 55 with the emission start threshold value. When the pixel value Vout has reached the emission start threshold value, the start of X-ray emission is detected (S203). Upon detecting the start of X-ray emission, the TFTs 46 of the normal pixels 40 are turned off to start the charge accumulation operation of the FPD 26 (S204).

Figure 6:
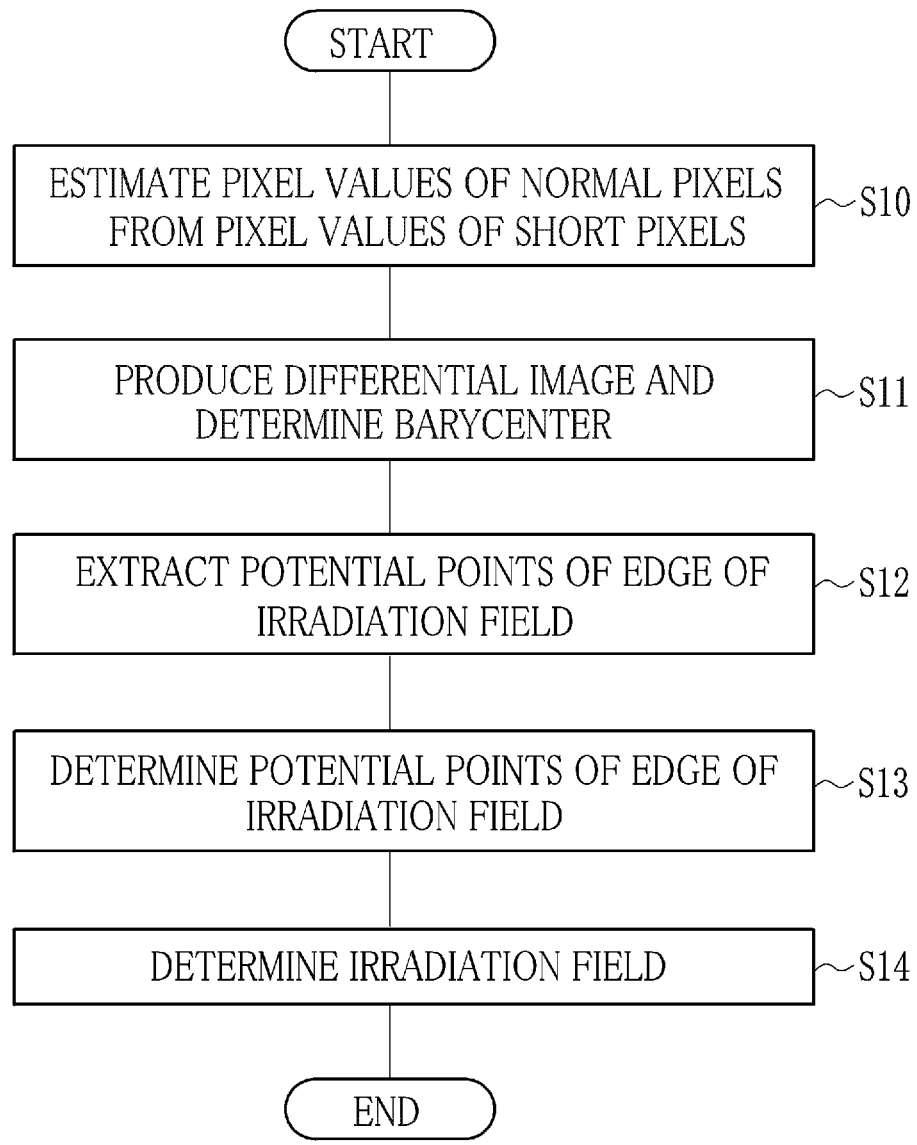
FIG. 6 is a flowchart of an irradiation field determination process.

The exposure controller 32 carries out AEC based on the pixel values Vout of the short pixels 55 (S205). In AEC, the irradiation field determiner 57 determines the irradiation field based on the pixel values Vout of the short pixels 55. To be more specific, as shown in FIG. 6, the pixel value estimator 61 estimates the pixel value of every normal pixel 40 arranged in the image capturing field 41 based on the pixel values Vout of the short pixels 55. The irradiation field determiner 57 determines the irradiation field based on the estimated pixel values of the normal pixels 40. Then, as shown in FIG. 11, the pixel determiner 58 determines the directly exposed area, the implant area, and the object area based on the estimated pixel values of the normal pixels 40 located within the irradiation field. The pixel determiner 58 chooses the normal pixels 40 having the minimum estimated pixel value and the maximum estimated pixel value from the normal pixels 40 located within the object area. The chosen normal pixel 40 having the minimum estimated pixel value is set as the minimum-value pixel. The chosen normal pixel 40 having the maximum estimated pixel value is set as the maximum-value pixel.

The coordinate data of the minimum-value pixel and the maximum-value pixel is inputted to the comparator 59 and the pixel value estimator 61. Whenever the pixel values Vout of the short pixels 55 are sampled, the pixel value estimator 61 estimates the pixel values of the minimum-value and maximum-value pixels based on the pixel values Vout, and inputs the estimated pixel values to the comparator 59. The comparator 59 integrates the estimated pixel values to obtain the first integrated value of the minimum-value pixel and the second integrated value of the maximum-value pixel. Also, as shown in FIG. 15, the first and second threshold values are set up in the comparator 59.

Referring to FIG. 15, the comparator 59 compares the second integrated value with the second threshold value, and compares the first integrated value with the first threshold value. The comparator 59 repeats the comparison between the first integrated value and the first threshold value, until the second integrated value reaches the second threshold value. When the first integrated value has reached the first threshold value, the comparator 59 issues the emission stop signal. When the second integrated value has reached the second threshold value, the comparator 59 issues the emission stop signal, even if the first integrated value has not reached the first threshold value.

The emission stop signal is transmitted from the electronic cassette 13 to the source controller 17 through the console 14 (S103). Upon receiving the emission stop signal, the source controller 17 issues the emission stop command to the X-ray source 16 to stop the X-ray emission (S303).

The emission start/stop detector 60 of the exposure controller 32 compares the pixel value Vout of the short pixel 55 with the emission stop threshold value. When the pixel value Vout has reached the emission stop threshold value, the stop of X-ray emission is detected (S206). Upon detecting the stop of X-ray emission, the FPD 26 stops the charge accumulation operation and starts the readout operation (S207). The X-ray image data read out from the FPD 26 is transmitted from the electronic cassette 13 to the console 14 (S208). The X-ray image data is subjected to the predetermined image processing, and written to the image storage 77 (S104).

The emission start/stop detector 60 is provided in this embodiment so that the FPD 26 detects the start and stop of X-ray emission, but the emission start/stop detector 60 may be omitted. In the case of the absence of the emission start/stop detector 60, the X-ray generating apparatus 11 transmits the start and stop of X-ray emission to the FPD 26 by electrical communication.

As described above, the minimum-value pixel having the lowest pixel value is chosen from the pixels in the image capturing field 41, and the first integrated value of the minimum-value pixel is compared with the necessary dose in AEC. Since the pixel is used as an AEC sensor for measuring the X-ray dose, it is possible to obtain higher spatial resolution than that of a conventional AEC sensor. Thus, a part of the object area can be assigned as reference of AEC. A pixel for use in AEC is chosen from the pixels in the image capturing field 41, so AEC is appropriately carried out even if the size and shape of the body portion is changed. Moreover, since the minimum-value pixel having the lowest pixel value is used for AEC, the necessary dose is certainly applied to the entire object area, and hence the image quality of the entire object area is improved.

Using the pixel provided in the image capturing field 41 for AEC can eliminate the need for providing the AEC sensor independent of the FPD 26, and hence simplify the structure of the apparatus. In the case of providing the AEC sensor independent of the FPD 26 in front of the image capturing field 41 of the FPD 26, the AEC sensor attenuates the X-rays applied to the FPD 26, but the present invention is free from such an attenuation problem.

In the above embodiment, the short pixels 55 and the normal pixels 40 have approximately the same structure and the same sensitivity to the X-rays, and therefore the pixel values of the normal pixels 40 are estimated with high accuracy based on the pixel values of the short pixels 55. This facilitates improving the accuracy of AEC. Also, the same or similar structure of the pixels can ease manufacturing and reduce manufacturing costs.

In the above embodiment, the maximum-value pixel is chosen in addition to the minimum-value pixel. When the second integrated value of the maximum-value pixel has reached the second threshold value, the X-ray emission is stopped even if the first integrated value of the minimum-value pixel has not reached the first threshold value. Therefore, it is possible to prevent the excessive X-ray exposure in the entire object area.

In the above embodiment, before setting the minimum-value and maximum-value pixels, the irradiation field is determined in the image capturing field 41, and the object area is determined in the irradiation field by excluding the directly exposed area and the implant area. The minimum-value and maximum-value pixels are chosen from the pixels of the object area. This allows setting the minimum-value and maximum-value pixels appropriately in the object area.

In the above embodiment, both the directly exposed area and the implant area are excluded from the irradiation field to determine the object area, and the minimum-value and maximum-value pixels are set in the object area. However, only the implant area may be excluded from the irradiation field, and the minimum-value and maximum-value pixels may be set in an area including the directly exposed area and the object area. In this case, the maximum-value pixel is probably chosen from the pixels in the directly exposed area. Using this maximum-value pixel, a maximum X-ray dose applied to the irradiation field is checked, and therefore it is possible to prevent the excessive X-ray exposure of the patient.

Without determination of the object area, an index area may be assigned in advance in the image capturing field 41, and the minimum-value and maximum-value pixels may be chosen from the pixels in the index area. In a case that the position, size, shape, and the like of areas where to locate the minimum-value and maximum-value pixels within the object area are roughly known, the assignment of the index area can eliminate the need for determining the irradiation field, the object area, and the like. The exposure controller 32 can determine the minimum-value and maximum-value pixels in the index area, so it is possible to ease calculation processing and accelerate processing speed for determining the minimum-value and maximum-value pixels.

In addition to the index area, an interest area may be assigned. In this case, for example, the exposure controller 32 sets the minimum-value pixel in the index area, and the maximum-value pixel in the interest area. This is effective when the X-ray transmittance is higher in the interest area than in the other areas in the object area, as in the case of the chest radiography described above. For example, in FIG. 14, the area 73a including the lung fields is assigned as the interest area, while the area 73b including the mediastinum and the diaphragm having the lower X-ray transmittance than that of the lung fields is assigned as the index area. This brings about the same effect as the above embodiment. Furthermore, eliminating the need for determining the object area increases the processing speed.

The index area and the interest area are assigned by the operation of the console 14, for example. An area setting screen that schematically shows the image capturing field 41 is displayed on the monitor 75 of the console 14, and an arbitrary area is assigned on the screen as the index area and the interest area. Data of the assigned index area and interest area is transmitted to the exposure controller 32 of the electronic cassette 13.

In the above embodiment, both of the minimum-value and maximum-value pixels are determined and AEC is performed based on the first and second integrated values. However, only the minimum-value pixel is determined and AEC may be performed based on only the first integrated value. If AEC is performed based on only the first integrated value, the necessary dose is certainly applied, so AEC is carried out appropriately. As for prevention of the excessive X-ray exposure, instead of determination of the maximum-value pixel, for example, maximum emission time may be determined and the X-ray emission may be forcefully stopped when a lapse of the maximum emission time has counted by a timer. As a matter of course, in a method of setting the maximum-value pixel, the X-ray dose applied to the object area is actually measured. Thus, the method of setting the maximum-value pixel prevents the excessive X-ray exposure more effectively than the method of setting the maximum emission time.

In the above embodiment, the short pixel 55 that is directly connected to the signal line 49 is used as the detection pixel for detecting the X-rays. However, another type of detection pixel that is connected to the signal line 49 through the TFT being the switching element, as with the normal pixel 40, may be provided instead. Using this type of detection pixel allows control of charge accumulation time of the detection pixel, and readout of the pixel value Vout at arbitrary timing.

In the above embodiment, the short pixels 55 are arranged together with the normal pixels 40, and the pixel values of the normal pixels 40 are estimated based on the pixel values Vout of the short pixels 55. However, instead of the short pixels 55, X-ray sensors that function similarly to the short pixels 55 may be provided such that each X-ray sensor is disposed between the normal pixels 40 adjoining to each other, in order to estimate the pixel values of the normal pixels 40 based on dose detection values of the X-ray sensors. The X-ray image read out after completion of the X-ray emission has a defect caused by the short pixels 55, which are dealt with as defective pixels. However, disposition of the X-ray sensors between the normal pixels 40 can eliminate the need for providing the short pixels 55 being the defect pixels, and therefore ease the defect correction.

Figure 17:
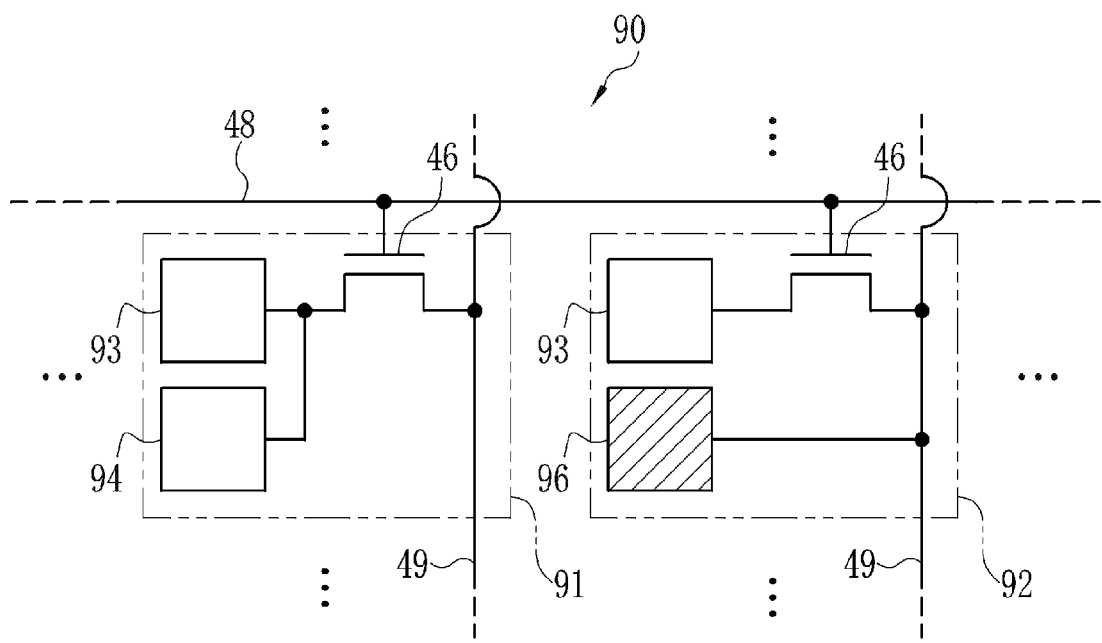
FIG. 17 is an explanatory view showing the structure of a detection pixel of another embodiment.

For the purpose of improving accuracy in the defect correction for correcting the effect of the short pixels 55 being the detection pixels, an FPD 90 shown in FIG. 17 is composed of two types of combined pixels 91 and 92, instead of the normal pixels 40 and the short pixels 55. The combined pixel 91 includes two subpixels 93 and 94. The combined pixel 92 includes two subpixels 93 and 96.

The subpixels 93 and 94 are specifically used for image detection as with the normal pixel 40, while the subpixel 96 is used for AEC as with the detection pixel such as the short pixel 55. Thus, the combined pixel 91 is constituted of the two subpixels 93 and 94 for use in the image detection, while the combined pixel 92 is constituted of the subpixel 93 for use in the image detection and the subpixel 96 functioning as the detection pixel. Each of the combined pixels 91 and 92 is approximately the same size as the single normal pixel 40. Each of the subpixels 93, 94, and 96 is approximately half of the single normal pixel 40 in size. The combined pixels 92 are distributed over the entire image capturing field 41 at an appropriate rate, as with the short pixels 55.

Each of the subpixels 93, 94, and 96 is made of a photodiode. In the combined pixel 91, the subpixels 93 and 94 are connected to the signal line 49 through the TFT 46 in parallel. In the combined pixel 92, on the other hand, the subpixel 93 is connected to the signal line 49 through the TFT 46, and the subpixel 96 is directly connected to the signal line 49 without through the TFT 46 just as with the short pixel 55.

In reading out the X-ray image, a sum of electric charge accumulated in the two subpixels 93 and 94 is read out from the combined pixel 91. From the combined pixel 92, only electric charge accumulated in the subpixel 93 is read out. The amount of electric charge accumulated in a subpixel is proportional to the size of the subpixel. Therefore, if the combined pixels 91 and 92 are applied with the same X-ray dose, the amount of the electric charge read out from the combined pixel 92 is approximately half of that from the combined pixel 91. Since the subpixel 96 is directly connected to the signal line 49, the electric charge produced in the subpixel 96 continuously flows into the signal line 49. The electric charge that flows from the subpixel 96 is detected as the pixel value Vout for use in AEC.

In the defect correction of the X-ray image, for example, a pixel value of the combined pixel 92 is doubled. In other words, the pixel value of the combined pixel 92 is multiplied by a coefficient that is calculated in advance based on the ratio in size between the subpixel 93 of the combined pixel 92 and the two subpixels 93 and 94 of the combined pixel 91. The defect correction is necessary even with the use of the combined pixels 92, owing to provision of the subpixels 96, which do not contribute detection of the X-ray image. However, as compared with the case of providing the short pixels 55, correction accuracy is improved due to the subpixels 93. For this reason, deterioration in the X-ray image is prevented, when compared with the above embodiment using the short pixels 55.

In the above embodiment, the pixel values of the normal pixels 40 are estimated based on the pixel values Vout of the short pixels 55 being the detection pixels, and the minimum-value and maximum-value pixels used in AEC are chosen from the normal pixels based on the estimated pixel values. However, the minimum-value and maximum-value pixels used in AEC may be chosen from the detection pixels. In this case, the first and second integrated values are obtained based on the pixel values Vout of the detection pixels. Since the detection pixels are distributed over the entire image capturing field 41 at the proper rate, AEC is appropriately carried out irrespective of the body portion to be imaged, even if the detection pixels and their pixel values Vout are directly used in AEC. The number of the detection pixels is less than that of the normal pixels 40, as a matter of course. Therefore, spatial positional accuracy deteriorates as compared with the case of choosing the pixels for use in AEC from the normal pixels 40, but accuracy in the pixel values themselves is improved because the measured pixel values are used instead of the estimated pixel values.

The FPD has the photodiodes and the TFTs formed in a glass substrate in this embodiment, but a CMOS (complementary metal oxide semiconductor) type FPD may be used instead. The CMOS type FPD has an image capturing field having an arrangement of pixels each of which is constituted of a photodiode and a switching element formed in a silicon substrate. The CMOS type FPD can perform so-called non-destructive readout in which while a pixel keeps holding electric charge, a voltage corresponding to the accumulated electric charge is read out from the pixel. Thus, every pixel is available as both the normal pixel for use in image detection and the detection pixel for use in AEC. In the case of using the CMOS type FPD, the exposure controller 32 performs determination of the object area, choice of the minimum-value and maximum-value pixels, and calculation of the first and second integrated values based on the measured pixel values, without estimating the pixel values.

In the above embodiment, the minimum-value pixel, which outputs the lowest pixel value, is set as the typical low-value pixel for use in AEC to obtain the X-ray image with favorable image quality. However, the minimum-value pixel may not be necessarily assigned as the typical low-value pixel, as long as the typical low-value pixel is determined from a plurality of low-value pixels including the minimum-value pixel. The plurality of low-value pixels refer to pixels that output a predetermined range of pixel values including the lowest pixel value, and more specifically, pixels that output pixel values within a range of lowest 10% to 20% in an entire range from the lowest pixel value to the highest pixel value. Taking the histogram of FIG. 12 as an example, out of the normal pixels 40 located within the object area, a plurality of normal pixels 40 whose estimated pixel values are within the range of lowest 10% to 20% are denoted as the low-value pixels.

The pixel determiner 58 determines the typical low-value pixel based on the histogram from the plurality of low-value pixels. As an example of determining the typical low-value pixel from the low-value pixels excluding the minimum-value pixel, for example, a low-value pixel that outputs a mean or median value may be determined as the typical low-value pixel. According to this method, even if the minimum-value pixel outputs an abnormal pixel value, the minimum-value pixel is not determined as the typical low-value pixel, so AEC is carried out appropriately. The pixel value of the determined typical low-value pixel is integrated, as in the case of the above embodiment, and an integrated value is used as the first integrated value.

A plurality of typical low-value pixels may be determined from the plurality of low-value pixels. In this case, for example, the pixel determiner 58 chooses one of the low-value pixels in the image capturing field 41, and then determines as the typical low-value pixels a pixel group that is composed of the chosen pixel and a plurality of low-value pixels around the chosen pixel. In a case where there are a plurality of typical low-value pixels, for example, a mean, median, or sum of the pixel values outputted from the typical low-value pixels is determined. The mean, median, or sum value is integrated and used as the first integrated value. The first threshold value to be compared with the first integrated value is appropriately determined in accordance with the type (mean, median, or sum) of the first integrated value.

The same goes for the typical high-value pixel used for prevention of the excessive X-ray exposure. To be more specific, the maximum-value pixel, which outputs the highest pixel value, is set as the typical high-value pixel in the above embodiment. However, the maximum-value pixel may not be necessarily assigned as the typical high-value pixel, as long as the typical high-value pixel is determined from a plurality of high-value pixels including the maximum-value pixel. The plurality of high-value pixels refer to pixels that output a predetermined range of pixel values including the highest pixel value, and more specifically, pixels that output pixel values within a range of highest 10% to 20% in the entire range from the lowest pixel value to the highest pixel value. Taking the histogram of FIG. 12 as an example, out of the normal pixels 40 located within the object area, a plurality of normal pixels 40 whose estimated pixel values are within the range of highest 10% to 20% are denoted as the high-value pixels.

The pixel determiner 58 determines the typical high-value pixel based on the histogram from the plurality of high-value pixels. The pixel value of the determined typical high-value pixel is integrated, as in the case of the above embodiment, and an integrated value is used as the second integrated value. According to this method, even if the maximum-value pixel outputs an abnormal pixel value, the maximum-value pixel is not determined as the typical high-value pixel, so AEC is carried out appropriately. A plurality of typical high-value pixels may be determined, as in the case of the typical low-value pixels. In this case, for example, a mean, median, or sum of the pixel values outputted from the plurality of typical high-value pixels is determined. The mean, median, or sum value is integrated and used as the second integrated value. The second threshold value to be compared with the second integrated value is appropriately determined in accordance with the type (mean, median, or sum) of the second integrated value.

Note that, how to determine the typical low-value and high-value pixels is not limited to above, and any method is usable as long as a relatively low-value pixel and a relatively high-value pixel in the image capturing field 41 are determined as the typical low-value and high-value pixels. For example, in order to prevent a defective pixel, which outputs an abnormal pixel value, from being set as the typical low-value or high-value pixel, the minimum-value pixel and the maximum-value pixel may be excluded from the low-value pixels and the high-value pixels, respectively. The typical low-value pixel is determined from the low-value pixels excluding the minimum-value pixel, and the typical high-value pixel is determined from the high-value pixels excluding the maximum-value pixel. In the case of determining both the typical high-value and low-value pixels, the most important matter is that AEC is performed with referring to both the relatively low-value and high-value pixels in the object area, for the purpose of obtaining the favorable image quality and preventing the excessive X-ray exposure. A slight difference in how to concretely determine the typical low-value and high-value pixels is inessential and has no influence on an effect of the present invention, though it only causes a small difference in the pixel values from the determined typical low-value and high-value pixels.

The electronic cassette 13 and the console 14 are wirelessly connected in the above embodiment, but may be connected through a wire. The console 14 and the electronic cassette 13 are separate in the above embodiment, but the console 14 may not be necessarily independent. The electronic cassette 13 may have the function of the console 14. Alternatively, another imaging control device specific to the control of the electronic cassette 13 may be provided between the electronic cassette 13 and the console 14, and the console 14 may take charge of only easy functions e.g. input of the imaging condition and display of the X-ray image. The console 14 and the source controller 17 may be integrated into one unit. The present invention may be applied to an installed type of X-ray image detecting device in which the FPD is contained in the imaging stand, instead of the electronic cassette being a portable type of X-ray image detecting device.

The present invention is applicable to a radiation imaging system using another type of radiation such as γ-rays instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging apparatus comprising:
    an image detector for detecting a radiographic image of an object, said image detector including a plurality of pixels arranged in an image capturing field, each of said pixels receiving radiation emitted from a radiation source and outputting a pixel value in accordance with a received radiation dose;
    a pixel determiner for determining at least one typical low-value pixel from said pixels based on said pixel values, and setting said typical low-value pixel as an exposure control pixel; and
    a comparator for comparing a first integrated value being an integrated value of said pixel value of said typical low-value pixel with a predetermined first threshold value, and performing radiation emission control such that, when said first integrated value has reached said first threshold value, said radiation source stops emitting said radiation,
    wherein
    said pixel determiner determines at least one typical high-value pixel from said pixels based on said pixel values, and sets said typical high-value pixel as another exposure control pixel, and
    said comparator compares a second integrated value being an integrated value of said pixel value of said typical high-value pixel with a predetermined second threshold value, and performs said radiation emission control such that, when said second integrated value has reached said second threshold value, said radiation source stops emitting said radiation even if said first integrated value has not reached said first threshold value.

2. The radiation imaging apparatus according to claim 1, further comprising:
    an irradiation field determiner for determining an irradiation field based on said pixel values, said irradiation field being a field irradiated with said radiation in said image capturing field, wherein
    said pixel determiner determines in said irradiation field a directly exposed area being an area applied with said radiation directly without through said object, an implant area being an area of an implant implanted in said object, and an object area being an area excluding said directly exposed area and said implant area from said irradiation field; and
    said typical low-value pixel and said typical high-value pixel are determined out of said pixels in said object area.

3. The radiation imaging apparatus according to claim 2, wherein said pixel determiner determines said object area based on a histogram of said pixel values of said pixels in said irradiation field.

4. The radiation imaging apparatus according to claim 1, wherein said pixel determiner determines said typical low-value pixel out of said pixels present within an index area, and said index area is predetermined in said image capturing field in accordance with a body portion to be imaged.

5. The radiation imaging apparatus according to claim 4, said pixel determiner determines said typical high-value pixel out of said pixels present within an interest area, and said interest area is predetermined in said image capturing field in accordance with said body portion to be imaged.

6. The radiation imaging apparatus according to claim 5, wherein radiation absorptance is higher in said index area than in said interest area.

7. The radiation imaging apparatus according to claim 1, wherein said pixels include a plurality of normal pixels for specific use in detection of said radiographic image, and a plurality of detection pixels distributed throughout said image capturing field to detect said radiation dose.

8. The radiation imaging apparatus according to claim 7, further comprising:
    a pixel value estimator for estimating said pixel value of said normal pixel based on said pixel values of said detection pixels near said normal pixel to be estimated; and
    said pixel determiner determines said typical low-value pixel and said typical high-value pixel based on said estimated pixel values.

9. The radiation imaging apparatus according to claim 8, wherein
    said image detector has a plurality of pixel groups each including one or more of said normal pixels and one or more of said detection pixels, and said detection pixels are laid out differently between said pixel groups adjoining to each other; and
    said pixel value estimator estimates said pixel value of said normal pixel of a first pixel group, based on said pixel value of said detection pixel belonging to said first pixel group and said pixel value of said detection pixel belonging to a second pixel group adjoining to said first pixel group.

10. The radiation imaging apparatus according to claim 7, wherein said pixel determiner determines said typical low-value pixel and said typical high-value pixel out of said detection pixels.

11. The radiation imaging apparatus according to claim 7, wherein
    signal lines electrically connected to said pixels are routed in said image capturing field to output said pixel values; and
    said detection pixel is connected to said signal line directly or through a switching element.

12. The radiation imaging apparatus according to claim 7, wherein said pixels include a combined pixel that is composed of a first subpixel functioning as said normal pixel and a second subpixel functioning as said detection pixel.

13. The radiation imaging apparatus according to claim 1, wherein said typical low-value pixel is a minimum-value pixel that outputs a lowest pixel value.

14. The radiation imaging apparatus according to claim 1, wherein
    said typical low-value pixel is a minimum-value pixel that outputs a lowest pixel value; and
    said typical high-value pixel is a maximum-value pixel that outputs a highest pixel value.

15. A radiation imaging system comprising:
(A) a radiation generating apparatus including:
a radiation source for emitting radiation to an object; and
a source controller for controlling operation of said radiation source; and
(B) a radiation imaging apparatus including:
an image detector for detecting a radiographic image of an object, said image detector including a plurality of pixels arranged in an image capturing field, each of said pixels receiving said radiation emitted from said radiation source and outputting a pixel value in accordance with an applied radiation dose;
a pixel determiner for determining at least one typical low-value pixel from said pixels based on said pixel values, and setting said typical low-value pixel as an exposure control pixel; and
a comparator for comparing a first integrated value being an integrated value of said pixel value of said typical low-value pixel with a predetermined first threshold value, and performing radiation emission control such that, when said first integrated value has reached said first threshold value, said radiation source stops emitting said radiation,
wherein
said pixel determiner determines at least one typical high-value pixel from said pixels based on said pixel values, and sets said typical high-value pixel as another exposure control pixel, and
said comparator compares a second integrated value being an integrated value of said pixel value of said typical high-value pixel with a predetermined second threshold value, and performs said radiation emission control such that, when said second integrated value has reached said second threshold value, said radiation source stops emitting said radiation even if said first integrated value has not reached said first threshold value.

16. A control method of a radiation imaging apparatus having an image detector for detecting a radiographic image of an object, said image detector including a plurality of pixels arranged in an image capturing field, each of said pixels receiving radiation emitted from a radiation source and outputting a pixel value in accordance with a received radiation dose, said control method comprising the steps of:
determining at least one typical low-value pixel from said pixels based on said pixel values, and setting said typical low-value pixel as an exposure control pixel; and
comparing a first integrated value being an integrated value of said pixel value of said typical low-value pixel with a predetermined first threshold value, and performing radiation emission control such that, when said first integrated value has reached said first threshold value, said radiation source stops emitting said radiation,
wherein
said determining step determines at least one typical high-value pixel from said pixels based on said pixel values, and sets said typical high-value pixel as another exposure control pixel, and
said comparing step compares a second integrated value being an integrated value of said pixel value of said typical high-value pixel with a predetermined second threshold value, and performs said radiation emission control such that, when said second integrated value has reached said second threshold value, said radiation source stops emitting said radiation even if said first integrated value has not reached said first threshold value.

* * * * *